(12) United States Patent
Despa et al.

(10) Patent No.: US 9,700,674 B2
(45) Date of Patent: Jul. 11, 2017

(54) INJECTION DEVICE CONFIGURED TO MATE WITH A MOBILE DEVICE

(71) Applicant: Becton, Dickinson and Company, Franklin Lakes, NJ (US)

(72) Inventors: Mircea Stefan Despa, Cary, NC (US); Sundeep Kankanala, Chapel Hill, NC (US); Dylan Wilson, Pittsboro, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 132 days.

(21) Appl. No.: 14/530,297

(22) Filed: Oct. 31, 2014

(65) Prior Publication Data

US 2015/0126963 A1 May 7, 2015

Related U.S. Application Data

(60) Provisional application No. 61/898,936, filed on Nov. 1, 2013.

(51) Int. Cl.
*A61M 5/20* (2006.01)
*G06F 19/00* (2011.01)
(Continued)

(52) U.S. Cl.
CPC .............. *A61M 5/20* (2013.01); *A61B 5/4839* (2013.01); *A61M 5/14244* (2013.01);
(Continued)

(58) Field of Classification Search
CPC ............ A61B 2560/045; A61B 5/0022; A61B 5/0077; A61B 5/0404; A61B 5/14532;
(Continued)

(56) References Cited

U.S. PATENT DOCUMENTS 7,390,319 B2   6/2008   Friedman
7,591,801 B2 *  9/2009   Brauker ............... A61B 5/0002
                                                  604/161

(Continued)

FOREIGN PATENT DOCUMENTS

WO   WO 2012/130901 A1   10/2012

OTHER PUBLICATIONS

Elder, Melissa, (Sep. 2011), "Wireless opportunities in Healthcare: A Kalorama Information Market Intelligence Report", Wireless Technologies in Healthcare, Kalorama Information, a division of MarketResearch.com, New York, pp. 1-246.
(Continued)

*Primary Examiner* — Quynh-Nhu H Vu
(74) *Attorney, Agent, or Firm* — Knobbe, Martens, Olson & Bear, LLP

(57) ABSTRACT

Injection systems powered, controlled and network-enabled by a mobile device, and methods for powering and controlling an injection system using a mobile device, are disclosed. An injection device includes a fluid container having a fluid container exit port, an injection driving element adapted to displace fluid from the fluid container through the fluid container exit port, and a connection module connected to the injection driving element, connectable to a mobile device, and adapted to receive electrical power or injection input data from the mobile device.

28 Claims, 18 Drawing Sheets

(51) Int. Cl.
*A61M 5/142* (2006.01)
*A61M 5/31* (2006.01)
*A61B 5/00* (2006.01)
*A61B 5/0205* (2006.01)
*A61B 5/021* (2006.01)
*A61B 5/0404* (2006.01)
*A61B 5/145* (2006.01)
*A61B 5/1455* (2006.01)
*A61B 5/15* (2006.01)
*A61B 5/157* (2006.01)
*A61M 5/145* (2006.01)
*A61M 5/172* (2006.01)

(52) U.S. Cl.
CPC ........ *G06F 19/322* (2013.01); *G06F 19/3406* (2013.01); *G06F 19/3456* (2013.01); *G06F 19/3468* (2013.01); *A61B 5/0022* (2013.01); *A61B 5/0077* (2013.01); *A61B 5/021* (2013.01); *A61B 5/02055* (2013.01); *A61B 5/0404* (2013.01); *A61B 5/14532* (2013.01); *A61B 5/14546* (2013.01); *A61B 5/14551* (2013.01); *A61B 5/157* (2013.01); *A61B 5/15087* (2013.01); *A61B 5/150786* (2013.01); *A61B 5/4887* (2013.01); *A61B 5/6898* (2013.01); *A61B 2560/045* (2013.01); *A61M 5/1452* (2013.01); *A61M 5/1723* (2013.01); *A61M 5/3146* (2013.01); *A61M 2205/215* (2013.01); *A61M 2205/33* (2013.01); *A61M 2205/3379* (2013.01); *A61M 2205/3553* (2013.01); *A61M 2205/3569* (2013.01); *A61M 2205/52* (2013.01); *A61M 2205/6054* (2013.01); *A61M 2205/6072* (2013.01); *A61M 2230/04* (2013.01); *A61M 2230/201* (2013.01); *A61M 2230/205* (2013.01); *A61M 2230/30* (2013.01); *A61M 2230/50* (2013.01)

(58) Field of Classification Search
CPC .......... A61B 5/14546; A61B 5/150786; A61B 5/15087; A61B 5/157; A61B 5/4839; A61B 5/4887; A61B 5/6898; A61M 2205/215; A61M 2205/33; A61M 2205/3379; A61M 2205/3553; A61M 2205/3569; A61M 2205/52; A61M 2205/6054; A61M 2205/6072; A61M 5/14244; A61M 5/1452; A61M 5/1723; A61M 5/20

See application file for complete search history.

(56) References Cited

U.S. PATENT DOCUMENTS

| | | | |
|---|---|---|---|
| 8,639,288 B1* | 1/2014 | Friedman | A61M 5/20 |
| | | | 455/556.1 |
| RE44,804 E | 3/2014 | Osborn et al. | |
| 9,336,353 B2* | 5/2016 | Valdes | |
| 2004/0215492 A1 | 10/2004 | Choi | |
| 2007/0293820 A1 | 12/2007 | Dacquay et al. | |
| 2008/0020794 A1* | 1/2008 | Garon | A61B 5/14532 |
| | | | 455/556.1 |
| 2008/0077081 A1* | 3/2008 | Mounce | A61M 5/1413 |
| | | | 604/67 |
| 2008/0091175 A1 | 4/2008 | Frikart et al. | |
| 2008/0262469 A1 | 10/2008 | Brister et al. | |
| 2008/0306434 A1* | 12/2008 | Dobbles | A61B 5/0002 |
| | | | 604/66 |
| 2008/0306444 A1 | 12/2008 | Brister et al. | |
| 2010/0292635 A1 | 11/2010 | Sundar | |
| 2011/0213299 A1 | 9/2011 | Cronenberg | |
| 2012/0094728 A1* | 4/2012 | Lee | G06F 1/1635 |
| | | | 455/572 |
| 2013/0053820 A1* | 2/2013 | Estes | A61M 5/1413 |
| | | | 604/504 |
| 2013/0245545 A1* | 9/2013 | Arnold | A61M 5/1723 |
| | | | 604/66 |
| 2014/0358112 A1* | 12/2014 | Smith | A61M 5/14244 |
| | | | 604/500 |
| 2015/0201880 A1* | 7/2015 | Bureau | A61M 37/0015 |
| | | | 600/301 |

OTHER PUBLICATIONS

Friedman, Steven, (Apr. 10, 2012), MedinCase Investor Presentation, Medavie Technologies.
Saint, Sean, (Dec. 2013), Overview Presentation, Companion Medical.
International Search Report and Written Opinion from International Patent Application No. PCT/US2014/063519 dated Feb. 11, 2015.

* cited by examiner

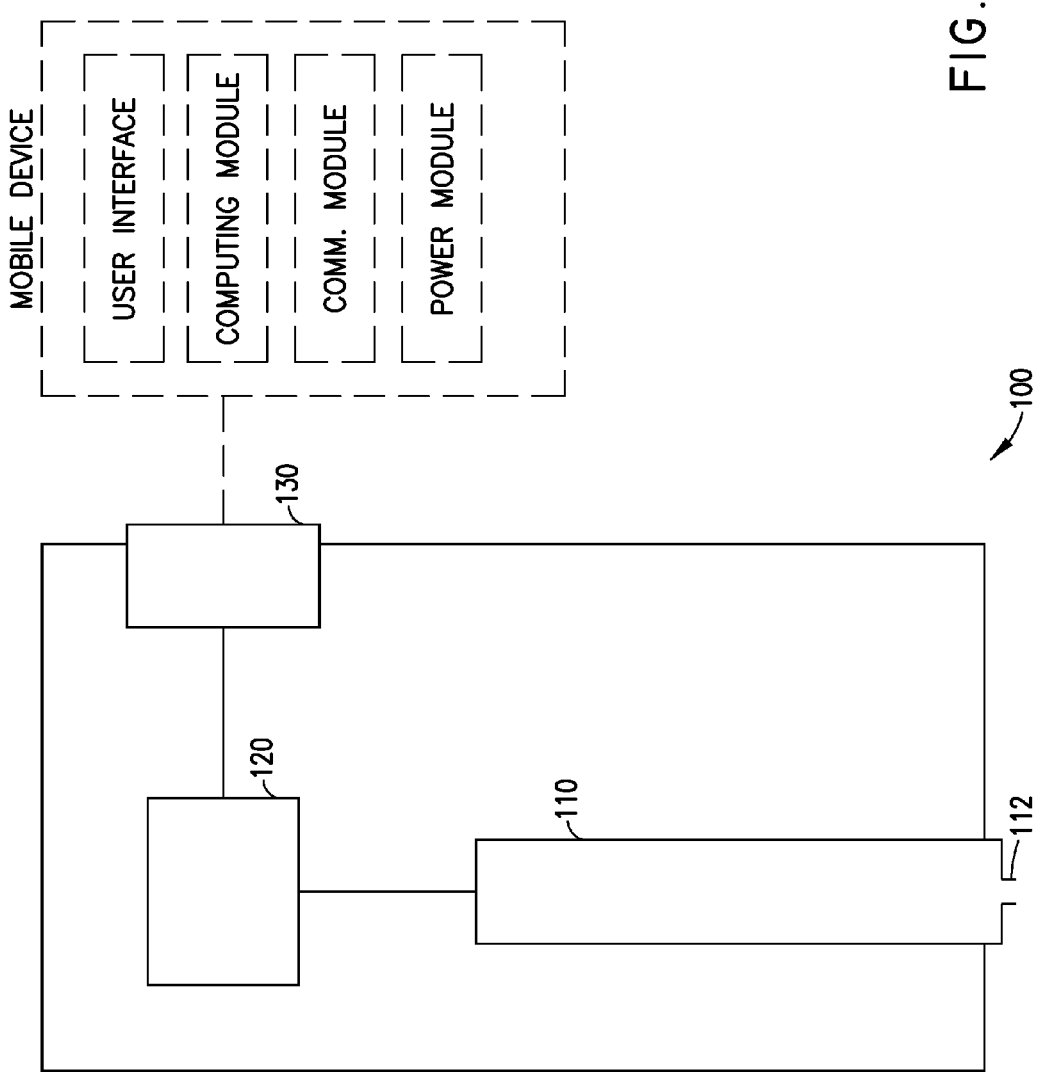

INJECTION DEVICE CONFIGURED TO MATE WITH A MOBILE DEVICE

CROSS-REFERENCE TO RELATED APPLICATIONS

This application claims priority to U.S. Provisional Patent Application Ser. No. 61/898,936 filed on Nov. 1, 2013 and entitled "Injection System Powered, Controlled and Network-Enabled By Mobile Device", the content of which is hereby incorporated by reference in its entirety.

FIELD OF THE INVENTION

The present invention relates generally to injection systems powered, controlled and network-enabled by a mobile device, and methods, including informatics/analytics, for powering and controlling an injection system using a mobile device.

BACKGROUND OF THE INVENTION

In certain circumstances, it is desirable to inject medication directly into human tissue in a user's home or in a public place. In the contemporary art, a user can inject medicament from a mechanically driven or actuated injection device. Injectors and prefilled syringes currently on the market, which are generally mechanically driven and actuated, require dexterity and strength that many users lack due to progression of the disease under treatment, such as Rheumatoid Arthritis or Multiple Sclerosis.

Conventional motorized and electronically actuated injection devices generally necessitate dedicated on-board modules such as power, computing, processing, sensing, imaging, diagnostics, or communication modules, which add bulk, weight, cost and complexity. Such devices lack portability and are undesirable to a user needing to discreetly inject medication in a public place. Additionally, it is increasingly common for users to carry smartphones or other mobile devices used for communication or entertainment, at all times.

Moreover, in certain circumstances, it is desirable to use an injection device that is connected to a network, for example to communicate treatment or patient-related data to an external device, or to provide connectivity between the user and stakeholders in the healthcare and patient management ecosystem, for example to ensure treatment is adhered to and administered appropriately. Conventional network-enabled injection devices must either include an on-board communication module, or connect to a network or to a network-enabled device using a cable. Such configurations are typically bulky and heavy, and difficult to use, resulting in a device that lacks portability and discretion.

Furthermore, it is sometimes desirable to administer a dose at a specific time, and with a specific speed or rate. Existing devices lack such capabilities, as well as intelligence needed for higher levels of functionality, thus requiring the user to dial the dose, after calculations related to meal intake (as may be the case for insulin treatment) or as directed by their healthcare provider.

SUMMARY OF THE INVENTION

An aspect of embodiments of the present invention is an injection device that can be motorized and network-enabled, and yet be small, light and discreet.

The foregoing and/or other aspects of the present invention are achieved by providing an injection device, including a fluid container having a fluid container exit port, an injection driving element adapted to displace fluid from the fluid container through the fluid container exit port, and a connection module connected to the injection driving element, connectable to a mobile device, and adapted to receive electrical power or injection input data from the mobile device.

The foregoing and/or other aspects of the present invention are achieved by providing a method of operating an injection device, including connecting a mobile device to the injection device, obtaining a recommended injection parameter from the mobile device, the recommended injection parameter calculated in accordance with at least one from the set of a patient vital data measurement value, a target patient vital data value and a user information value, inputting a desired injection parameter value into the mobile device, transmitting a signal indicative of at least one injection parameter from the mobile device to the injection device, performing an injection with the injection device in accordance with the signal indicative of at least one injection parameter, and obtaining an administered injection parameter value.

One aspect is an injection device that includes an injection driving element capable of displacing fluid from a fluid container through a fluid container exit port; a housing at least partially enclosing the injection driving element; a connection module electrically connected to the injection driving element and configured to receive electrical power and data from a mobile device; and a mount configured to mate with the mobile device.

Another aspect is a combination of the aforementioned injection device with a mobile device connected to the through the mount.

Yet another aspect is a method of operating a injection device, that includes providing a mobile device mated to the injection device; obtaining a recommended injection parameter from the mobile device, the recommended injection parameter calculated in accordance with at least one from the set of a patient vital data measurement value, a target patient vital data value and a user information value; receiving a desired injection parameter value into the mobile device; transmitting a signal indicative of at least one injection parameter from the mobile device to the injection device; activating an injection with the injection device in accordance with the signal indicative of at least one injection parameter; and obtaining an administered injection parameter value.

Still another aspect is a method of operating an injection device that is mated to a mobile device. This method includes sensing rotation of the injection device to a new orientation; transmitting a signal indicative of the new orientation of the injection device to the mobile device; and enabling an input on the mobile device if the rotation is determined to be to a predetermined orientation, wherein the input controls a function of the injection device.

Additional and/or other aspects and advantages of the present invention will be set forth in the description that follows, or will be apparent from the description, or may be learned by practice of the invention.

BRIEF DESCRIPTION OF THE DRAWINGS

The various objects, advantages and novel features of illustrative embodiments of the present invention will be more readily appreciated from the following detailed description when read in conjunction with the appended drawings, in which:

FIG. 1 is a schematic view of an injection device in accordance with an illustrative embodiment of the present invention;

DETAILED DESCRIPTION OF THE ILLUSTRATIVE EMBODIMENTS

Figure 2A:
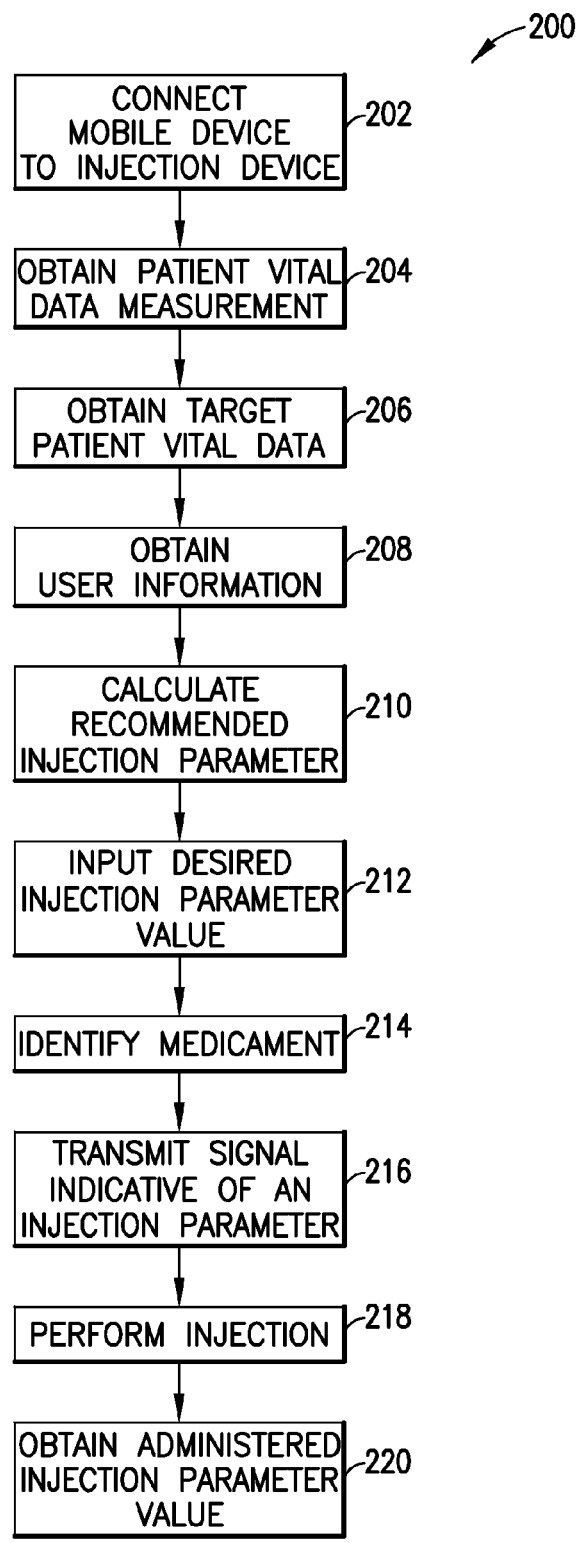
FIG. 2A is a schematic view of a method of operating an injection device in accordance with an illustrative embodiment of the present invention.

As will be appreciated by one skilled in the art, there are numerous ways of carrying out the examples, improvements, and arrangements of a medicament delivery device in accordance with embodiments of the present invention disclosed herein. Although reference will be made to the illustrative embodiments depicted in the drawings and the following descriptions, the embodiments disclosed herein are not meant to be exhaustive of the various alternative designs and embodiments that are encompassed by the disclosed invention, and those skilled in the art will readily appreciate that various modifications may be made, and various combinations can be made, without departing from the invention.

Although various persons, including, but not limited to, a patient or a healthcare professional, can operate or use illustrative embodiments of the present invention, for brevity an operator or user will be referred to as a "user" hereinafter.

Although various fluids can be employed in illustrative embodiments of the present invention, fluid in an injection device will be referred to as "medicament" hereinafter.

Although various methods of medicament administration, including, but not limited to, injection or infusion, can be implemented using illustrative embodiments of the present invention, for brevity a medicament administration will be referred to as an "injection" hereinafter.

Although various inputs, including, but not limited to, mechanical buttons, tactile inputs, voice-controlled input, or any other inputs known in the art, can be implemented using illustrative embodiments of the present invention, for brevity an input will interchangeably be referred to as a "button" or a "trigger" hereinafter. One skilled in the art will readily appreciate that a single button can perform the functions of multiple buttons by various combinations of presses, long-presses, "swiping," and other input methods known in the art.

Illustrative embodiments in accordance with the present invention are depicted in FIGS. 1-4. In an illustrative embodiment according to the present invention, an injection device is connected to a mobile device and can be used to inject medicament into a layer of tissue or other injection site. A mobile device includes any mobile device known in the art, including, but not limited to, a smartphone, a tablet computer, or any telecommunication device with computing ability, a mobile device connection module, and preferably an adaptable user interface such as, but not limited to a touchscreen. A user typically possesses a mobile device, which she can utilize for various functions, such as sending and receiving phone calls, sending and receiving text messages, and browsing the internet.

In an illustrative embodiment according to the present invention, the injection device is powered and controlled by the mobile device, and uses the mobile device to communicate relevant treatment or patient related data. Illustrative embodiments can be particularly advantageous to a user who already has and carries a mobile device that includes power, computing/processing, and communication modules. An illustrative injection device can therefore be simple, inexpensive and portable, need not include on-board power, computing/processing and communication modules, can utilize a power module, a communication module, a computing/processing module and a user interface of a mobile device, and can be used with ease by patients with diminishing motor abilities. The use of an illustrative injection device according to the present invention can also create opportunities for interactions between a user and her mobile device, can improve patient compliance to treatment, and can be more discreet than conventional injection devices.

FIG. 1 depicts a schematic view of an illustrative embodiment of an injection device 100 in accordance with the present invention. The injection device 100 includes a fluid container 110 having a fluid container exit port 112, an injection driving element 120 and a connection module 130. The injection driving element 120 is adapted to displace fluid from the fluid container 110 through the fluid container exit port 112.

In an illustrative embodiment according to the present invention, the connection module 130 is connectable to a mobile device, by wire or wireless connection. The connection module 130 is adapted to receive from the mobile device electrical power or injection input data. As a result, the injection device 100 need not include on-board power, computing/processing and communication modules, can utilize the power module, communication module, computing/processing module and user interface of a mobile device, and can be small, light, discreet and affordable. These features can enable a user with reduced physical strength or dexterity to easily, accurately and reliably perform an injection. One skilled in the art will readily appreciate that power, computing/processing and communication modules of a mobile device can include various combinations of hardware and software.

In an illustrative embodiment according to the present invention, the connection module 130 is connected to the injection driving element 120 to provide the injection driving element 120 with power or data.

In an illustrative embodiment according to the present invention, a mobile device includes a mobile device connection module connectable to the connection module 130. In an illustrative embodiment according to the present invention, the mobile device connection module of the mobile device is adapted to connect the injection driving element 120 of the injection device 100 to a power module or a computing module of the mobile device.

FIG. 2A depicts an illustrative embodiment of a method 200 of operating an injection device according to the present invention, which includes connecting a mobile device to the injection device at step 202, obtaining a patient vital data measurement value at step 204, obtaining a target patient vital data value at step 206, obtaining a user information value at step 208, calculating a recommended injection parameter in accordance with the patient vital data measurement value, the target patient vital data value and/or the user information value at step 210, inputting a desired injection parameter value into the mobile device at step 212, identifying a medicament identifier at step 214, transmitting a signal indicative of at least one injection parameter from the mobile device to the injection device at step 216, performing an injection with the injection device in accordance with the signal indicative of at least one injection parameter at step 218, and obtaining at least one administered injection parameter value at step 220. An injection parameter can include, but is not limited to, dosage setting, dose speed or rate setting, injection depth, and time of administration, or any injection-related or treatment-related parameter known in the art. In alternative illustrative embodiments, any combinations of these functions are also possible.

In an illustrative embodiment according to the present invention, patient vital data includes, but is not limited to, blood pressure, temperature, blood oxygen level, or blood glucose level. The patient vital data measurement value is measured using a sensor on the injection device or an external device, and is transmitted to the mobile device. For example, a blood glucose level value may be received by the mobile device from a continuous glucose monitor (CGM) or other blood glucose monitor (BGM).

In an illustrative embodiment according to the present invention, the target patient vital value is determined by the mobile device in accordance with a constant value or a process obtained from a healthcare professional.

In an illustrative embodiment according to the present invention, the user information value includes a calorie value. The calorie value is determined according to food items taken or about to be taken, selected from a list by the user. A calorie value list is stored on the mobile device, on the injection device, or on an external device connected to the mobile device, including, but not limited to a local or remote server. In an illustrative embodiment according to the present invention, the user information value includes any information pertaining to the user that is relevant to an injection.

In an illustrative embodiment according to the present invention, the caloric information is determined according to data from an activity tracker. An activity tracker can provide activity and/or caloric information about a patient, including, but not limited to, physical movements, exercise, sleep pattern, and caloric consumption information, or any other patient data that may affect a caloric value about the patient. For example, an activity tracker can be communicatively coupled, locally or remotely, with the mobile device.

In an illustrative embodiment according to the present invention, a medicament identifier is identified using a sensor of the mobile device, of the injection device, or of an external device connected to the mobile device. A medicament identifier can include any identifier known in the art, including, but not limited to, a barcode, a Quick Response (QR) code, a Radio-Frequency Identification (RFID) tag, a Near-Field Communication (NFC) tag, a label, or a temperature-sensitive label or tag. Sensors can include any suitable sensor known in the art, including, but not limited to, a camera or an NFC module. A medicament identifier is identified using a medicament database stored on the mobile device, on the injection device, or on an external device connected to the mobile device, including, but not limited to a local or remote server. In an illustrative embodiment according to the present invention, medicament identification is used by prescription tracking functions of a mobile device or of other devices connected to the mobile device. In an illustrative embodiment according to the present invention, a medicament database includes information on contraindications for a medicament. Information on contraindications can include, but are not limited to, information on administration of the medicament in conjunction with other medicaments or the intake of foods, information on administration time, with or without meal, or other recommendations specific to the medicament or generally related to the user's health. In an illustrative embodiment according to the present invention, the mobile device can notify a user of contraindications for a medicament. In an illustrative embodiment according to the present invention, the mobile device suggests alternative medicaments or treatment options to the user.

In an illustrative embodiment according to the present invention, a needle identifier is identified using a sensor of the mobile device, of the injection device, or of an external device connected to the mobile device. A needle identifier can include any identifier known in the art, including, but not limited to, a barcode, a Quick Response (QR) code, an RFID tag, a Near-Field Communication (NFC) tag, a label, or a temperature-sensitive label or tag. Sensors can include any suitable sensor known in the art, including, but not limited to, a camera or an NFC module. A needle identifier is identified using a needle database stored on the mobile device, on the injection device, or on an external device connected to the mobile device, including, but not limited to a local or remote server. In an illustrative embodiment according to the present invention, needle identification is used by prescription tracking functions of a mobile device or of other devices connected to the mobile device. Identifying a needle can assist in determining whether a needle has been used or is not the appropriate type of needle. In an illustrative embodiment according to the present invention, a user is notified by the mobile device if the needle has been used or, alternatively, is not the appropriate type of needle. In an illustrative embodiment according to the present invention, administration of a medicament is disabled by the mobile device if the needle has been used or, alternatively, is not the appropriate type of needle.

In an illustrative embodiment according to the present invention, injection-related information is obtained using an injection-related information sensor of the mobile device, of the injection device, or of an external device connected to the mobile device. Injection-related information includes, but is not limited to, dose, dose administration speed, needle insertion depth, needle insertion location, needle insertion time, injection pressure, and temperature at injection site.

In an illustrative embodiment according to the present invention, a mobile device uses the sensor and vital data as inputs and performs computational processes and the computing/processing module of the mobile device generates an injection dosage and an injection speed or rate with ease and high reliability. In an illustrative embodiment according to the present invention, the mobile device can adjust or modulate injection parameters and monitor injection diagnostics, according to user input, administration site location and condition, and/or the patient's level of comfort, to achieve a suitable injection event and outcome. An example of suitable outcome can be improved pharmacokinetics and pharmacodynamics due to optimization of insertion depth and injection rate. For example, injection parameters can include, but are not limited to, dosage setting, dose speed or rate setting, injection depth, and time of administration, or any injection-related or treatment-related parameter known in the art, and injection diagnostics can include, but are not limited to, recording of the dose administration progression and ending, and line pressure, or any other injection diagnostics known in the art.

In an illustrative embodiment according to the present invention, the injection is performed by a user following priming, penetration and/or injection instructions from the mobile device. A signal indicative of at least one injection parameter transmitted to the injection device can include, but is not limited to, a dose value, such as a desired dose input by the user, or any other injection parameter value. The injection device then translates the signal indicative of at least one injection parameter to signals indicative of control commands for a motor, including, but not limited to, a start command, a stop command, a direction command, and a speed command. Alternatively, the signal indicative of at least one injection parameter transmitted to the injection device includes control commands for a motor, which the mobile device has translated from an injection parameter value.

In an illustrative embodiment according to the present invention, the signal indicative of at least one injection parameter is transmitted from the mobile device to the injection device, after a user presses, long-presses, or presses and holds a transmittal trigger, so as to minimize the risk of accidental injections. The transmittal trigger can be located on the mobile device or on the injection device, and includes, but is not limited to, a mechanical button or a tactile input. Alternatively, transmittal of the signal is triggered by voice command. The injection is performed by the injection device after the signal is received by the injection device, automatically or after the user triggers the injection on the injection device.

In an illustrative embodiment according to the present invention, an injection timestamp value is determined by the mobile device, or is determined by the injection device and transmitted to the mobile device. If a device is turned off or communication is otherwise lost before a timestamp value or other data are communicated, data transmission is postponed until communication is reestablished.

In an illustrative embodiment according to the present invention, an administered injection parameter value is measured using a delivery sensor, including, but not limited to, an electric eye or a flow sensor, or using a penetration sensor. The delivery sensor can be located on the injection device, the mobile device, or an external device connected to the mobile device. The administered injection parameter value is transmitted to the mobile device. The mobile device then generates a report showing the desired injection parameter value, the administered injection parameter value, and the injection timestamp value. Other examples of data generated and communicated can include location and depth of insertion, or other sensor data collected at and around the time of injection. The report is sent to a healthcare provider, or to an external device. The healthcare provider or the external device can determine whether the administration of the medicament is in accordance with a treatment plan, and can communicate an indicator of this determination to the mobile device.

In an illustrative embodiment according to the present invention, a software application, as shown in FIGS. 2B-2G, performs or assists a user in performing multiple functions. For example, application functions can include, but are not limited to, information determining, user notification, dose dialing, injection, and medicament identification.

In an illustrative embodiment according to the present invention, a software application also provides instructions and feedback to the user during therapy, thereby providing the convenience of injection control and support using a single device. In an illustrative embodiment according to the present invention, a software application provides real-time instructions on proper use of the device or other aspects of the treatment, feedback or confirmation on how the device was used, and results of disease specific physical and/or neurological functional tests, which can be provided using features on the mobile device, to quantify a patient's disease state.

In an illustrative embodiment according to the present invention, a healthcare professional can provide live support to a user using a live communication function of a mobile device.

In an illustrative embodiment according to the present invention, visual data captured by a camera is processed by the phone using data aggregation and analytics. For example, the visual data can be indicative of a location of the injection site on a patient's body. In the case of an injection, the visual data can be indicative of a depth of injection to confirm intradermal, subcutaneous and intradermal delivery, which can affect pharmacokinetics/pharmacodynamics (PK/PD).

In an illustrative embodiment according to the present invention, the application can determine information relating to medicament administration scheduling, vital signs monitoring, food specific to a user's diet, and/or the location of health-related establishments, including, but not limited to, hospitals, pharmacies, and exercise facilities. In an illustrative embodiment according to the present invention, information relating to medicament administration scheduling, and food specific to a user's diet can be determined in accordance with stored parameters.

In an illustrative embodiment according to the present invention, the mobile device further assists a user with remembering the day and time of administration according to a planned administration schedule. Computing capabilities of the mobile device can be used to manage the schedule locally or via communications received from an external device, including, but not limited to, an external computer, a healthcare provider's office, or other data center.

Figure 2B:
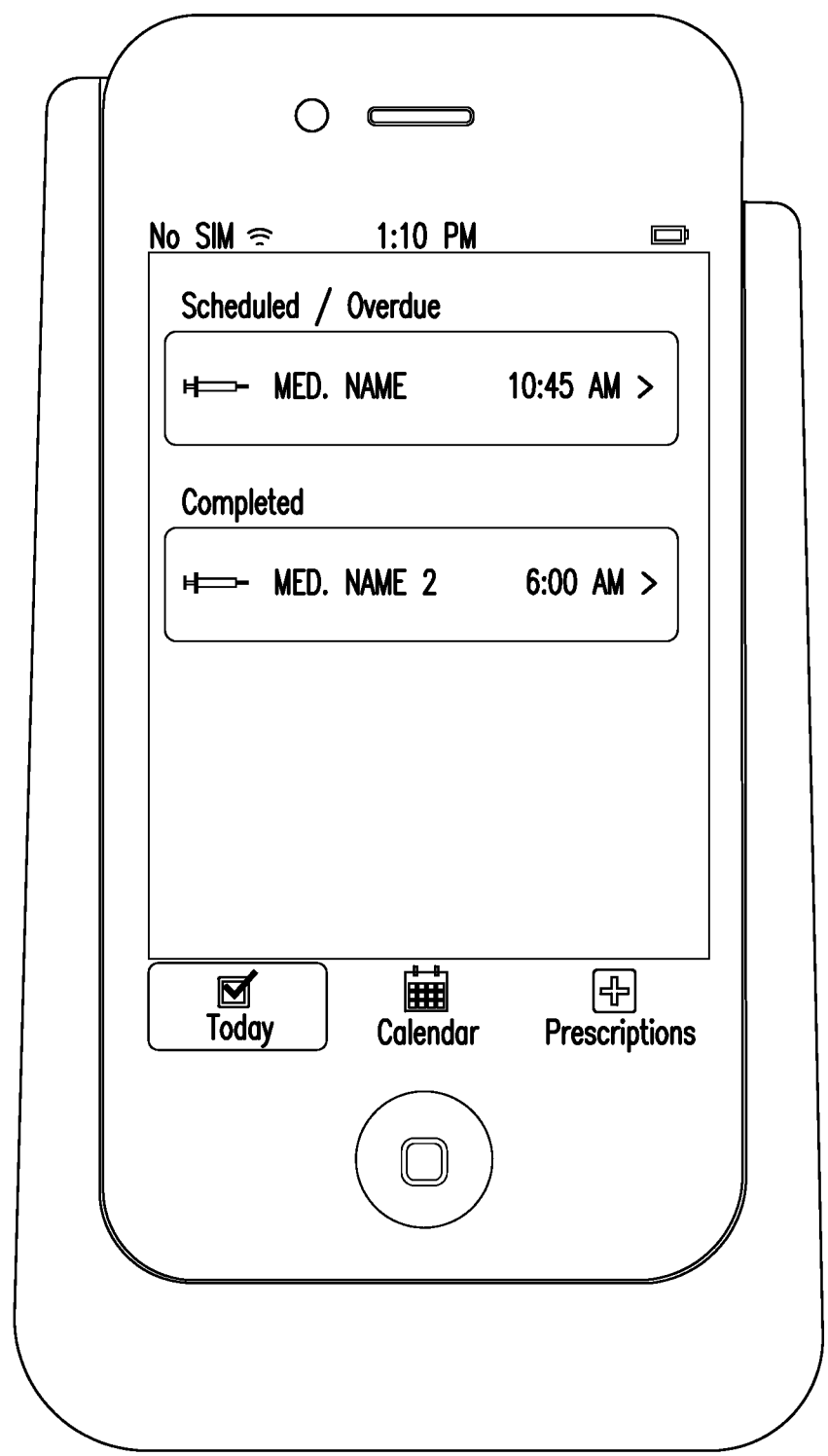
FIGS. 2B-2G show an injection device in combination with a mobile device with a software application, in accordance with an illustrative embodiment of the present invention.

In an illustrative embodiment according to the present invention, a software application, as shown in FIG. 2B, displays a schedule of medicament administrations. For example, administrations can be indicated as Scheduled/Overdue administrations, Completed administrations, and Oral Medications.

In an illustrative embodiment according to the present invention, vital signs can be monitored in accordance with data received from a vital sign sensor. For example, a notification can be generated if a user's vital signs reach a level above or below a threshold value, in accordance with stored parameters.

In an illustrative embodiment according to the present invention, information relating to the location of food specific to a user's diet, and the location of health-related establishments, can be determined in accordance with location information, for example, using a location-determining module of a mobile device. In an illustrative embodiment according to the present invention, information determined by the application can be accessed by the user upon user request, or can be presented to the user as a visual and/or audio notification on a mobile device. A location-determining module can use GPS technology, cellular signal triangulation, IP geo-location, or other location determination methods known in the art.

In an illustrative embodiment according to the present invention, the application can perform functions relating to dose dialing, including, but not limited to, setting injection parameters or obtaining injection diagnostics. For example, injection parameters can include, but are not limited to, dosage setting, dose speed or rate setting, injection depth, time of administration, or any other injection-related or treatment-related function. An injection parameter can be modulated by a user using a graphical user interface, including, but not limited to, inputting a numerical value or using a touch screen or other tactile input to adjust a virtual knob or slider. Alternatively, the application can set injection parameters accordance with stored parameters. Injection diagnostics can include, but are not limited to, recording of the dose administration progression and ending, and line pressure.

In an illustrative embodiment according to the present invention, the application can automatically start or stop an injection in accordance with stored parameters.

In an illustrative embodiment according to the present invention, a communication module of the mobile device can be connected to a network, for example to communicate injection, treatment or patient-related data to an external device, including, but not limited to a local or remote server, or to otherwise provide connectivity between the user or the injection device and stakeholders in the healthcare and patient management ecosystem, including, but not limited to doctors, nurses, pharmacists, family members and payors. In some instances, this can help ensure that a treatment is adhered to and administered appropriately. The communication module can be connected to a network by wired or wireless communication, cell communication, Bluetooth®, ZigBee®, LAN, WLAN, RF, IR, or any other communication method or system known in the art.

In an illustrative embodiment according to the present invention, a medicament identifier of a medicament to be administered, including, but not limited to, a medicament name or associated number or e-pedigree information, is searched in a device-local database or communicated to an external device by the mobile device. The information found locally or remotely can then determine whether the administered medicament is in accordance with a treatment plan, and can communicate an indicator of this determination to the mobile device.

Figure 2C:
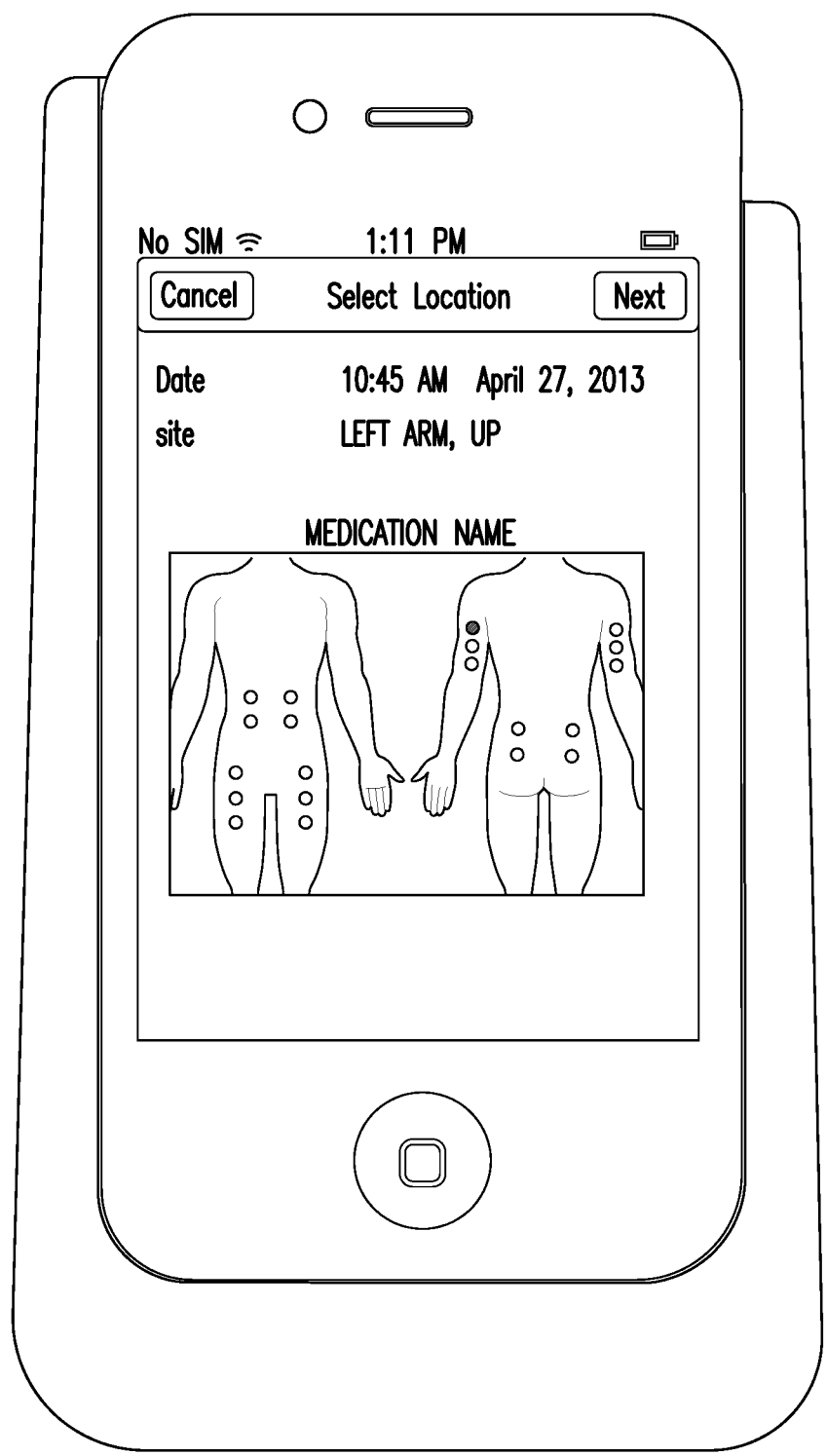

In an illustrative embodiment according to the present invention, medicament delivery location information is communicated to an external device by the mobile device. This information can be input by a user into a software application by selecting a region of the body on a body map, as shown in FIG. 2C. The external device can then determine whether the delivery location is in accordance with a treatment plan, and can communicate an indicator of this determination to the mobile device. This information can also be used by a healthcare professional or a software application to determine a patient's preference for a particular injection site, or to suggest injection site rotation cycles to the user during future administrations.

In an illustrative embodiment according to the present invention, a software application, as shown in FIG. 2C, displays administration locations mapped on a human body. For example, a map can display scheduled administration locations, and can be used by a user to select an administration location.

Figure 2D:
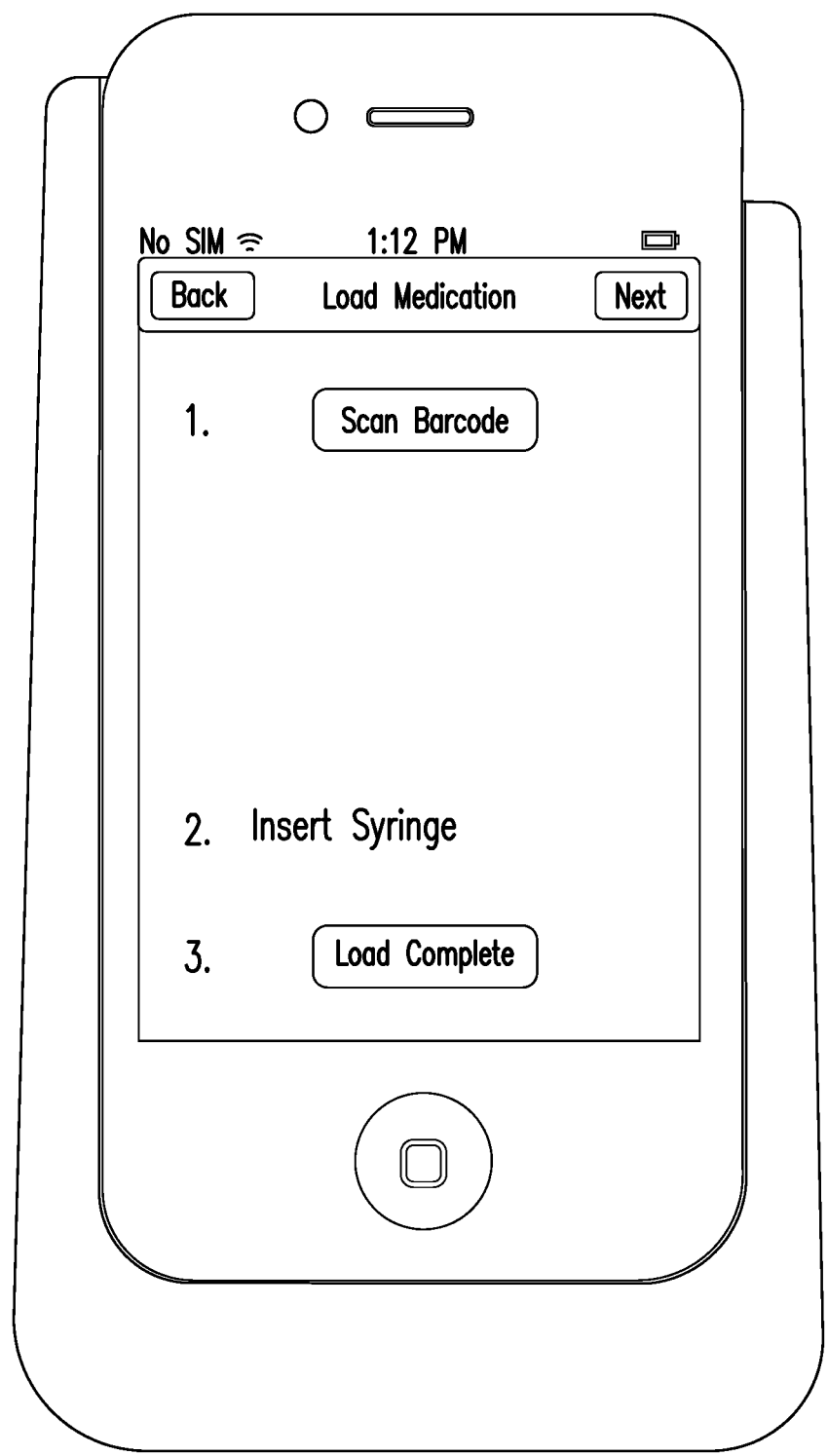

In an illustrative embodiment according to the present invention, a software application, as shown in FIG. 2D, displays a series of steps guiding a user through a medicament loading procedure. For example, a medicament identification function can be enabled at a first step, a user can be directed to insert a syringe at a second step, and a user can be indicated to load a medication cartridge at a third step.

Figure 2E:
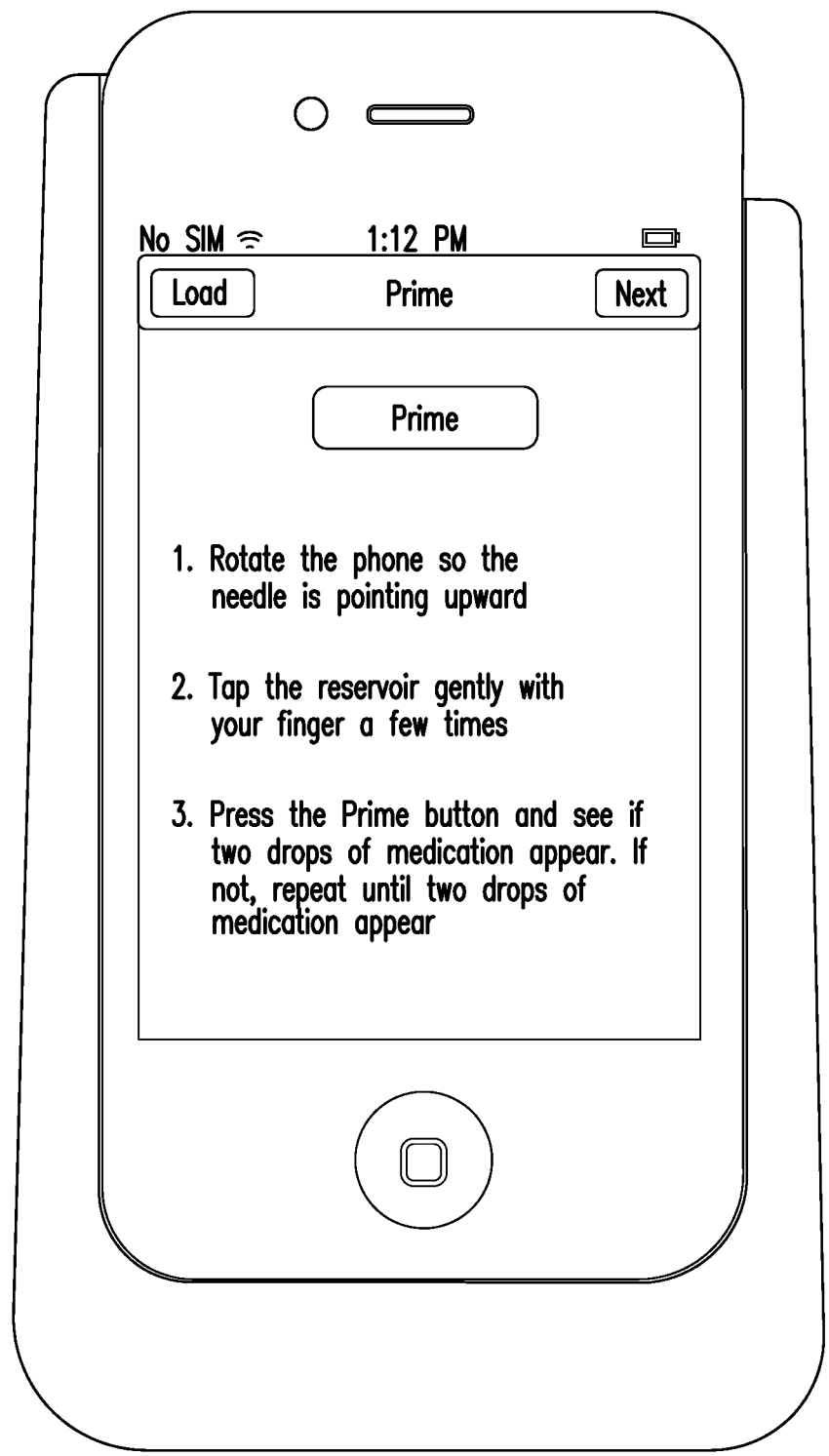

In an illustrative embodiment according to the present invention, a software application, as shown in FIG. 2E, displays a series of steps guiding a user through a medicament priming procedure. For example, a user can be directed to point the mobile device upward at a first step, the user can be directed to tap a medicament reservoir at a second step, and the user can be indicated to press a prime button at a third step.

Figure 2F:
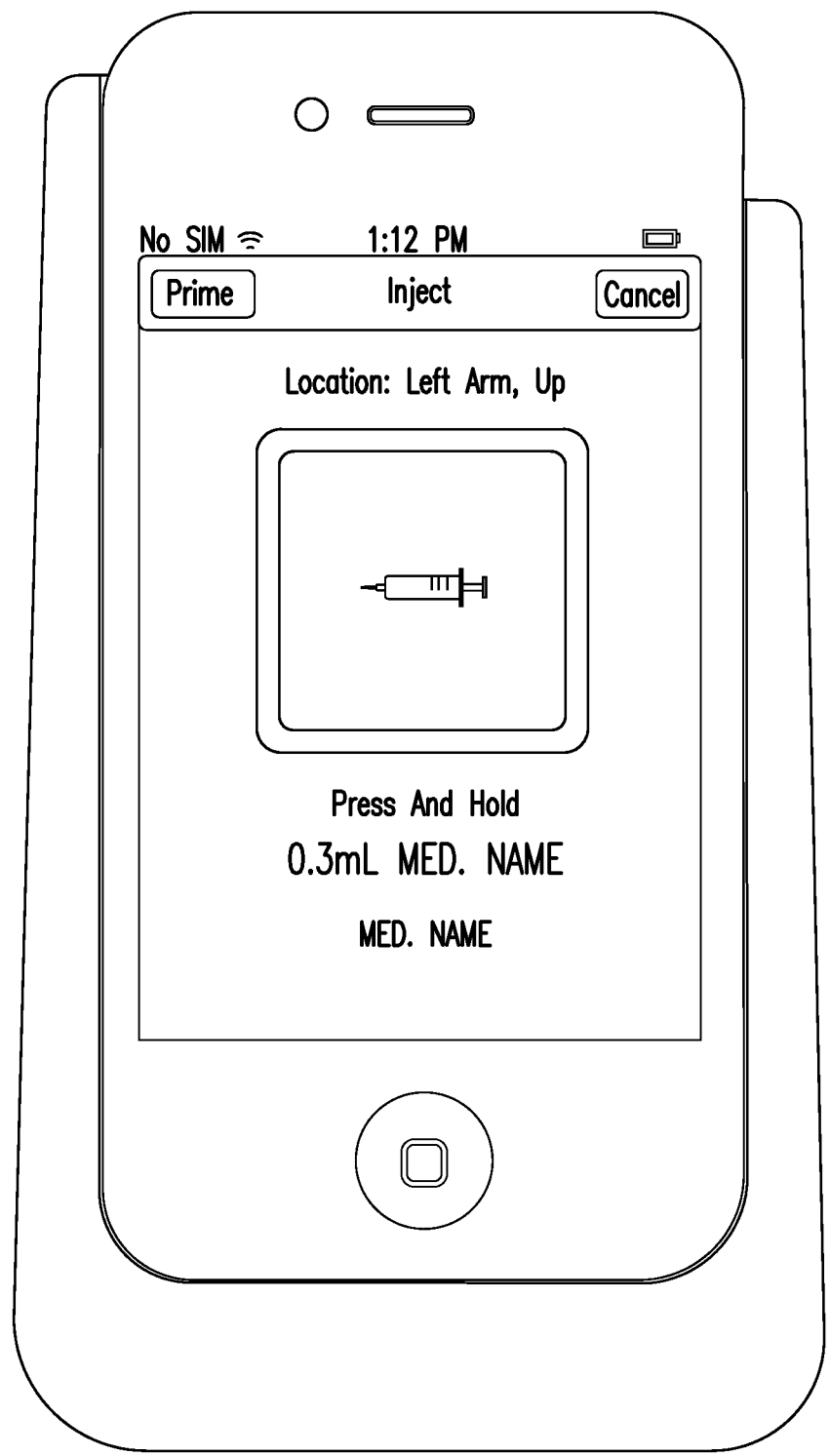

In an illustrative embodiment according to the present invention, a software application, as shown in FIG. 2F, displays a series of steps guiding a user through a medicament injection procedure. For example, an injection location, a medicament name and a medicament dose can be displayed, and a user can be directed to press and hold a touchscreen button to dispense the medicament.

Figure 2G:
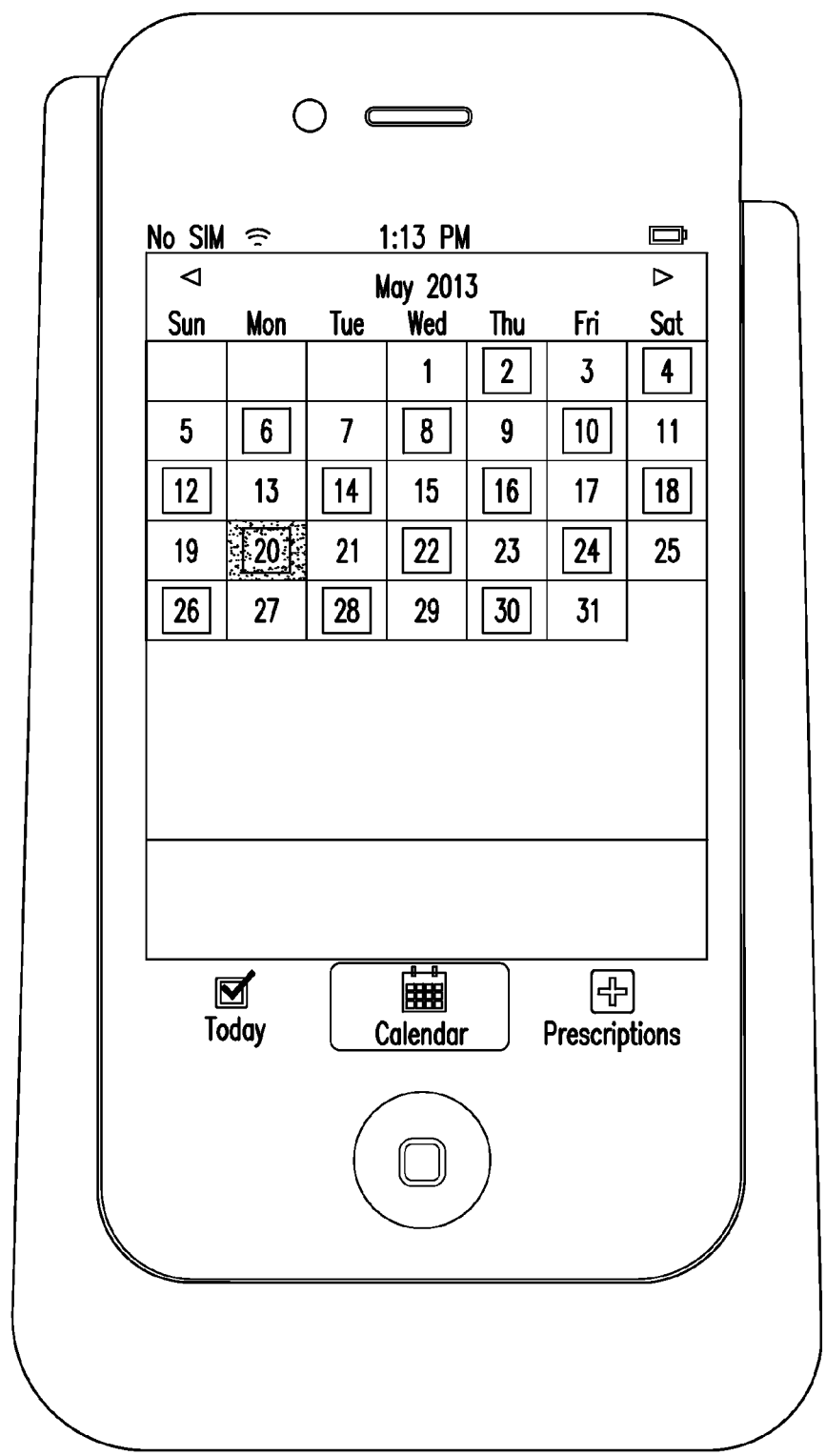

In an illustrative embodiment according to the present invention, a software application, as shown in FIG. 2G, displays an injection schedule. For example, a calendar screen can display past and future injection days, and an indication that a user missed an injection. The injection schedule can also provide options for recording injections or scheduling alarms.

In an illustrative embodiment according to the present invention, a software application operates with more than one injection device. A user can switch between devices using a graphical user interface of the application. Alternatively, the software application can be configured to assign control priority to a newly connected device, or to a particular type of device, such as one connected by sleeve connection. A graphical user interface of the software application can change as a function of which injection device it is operating.

Figure 3A:
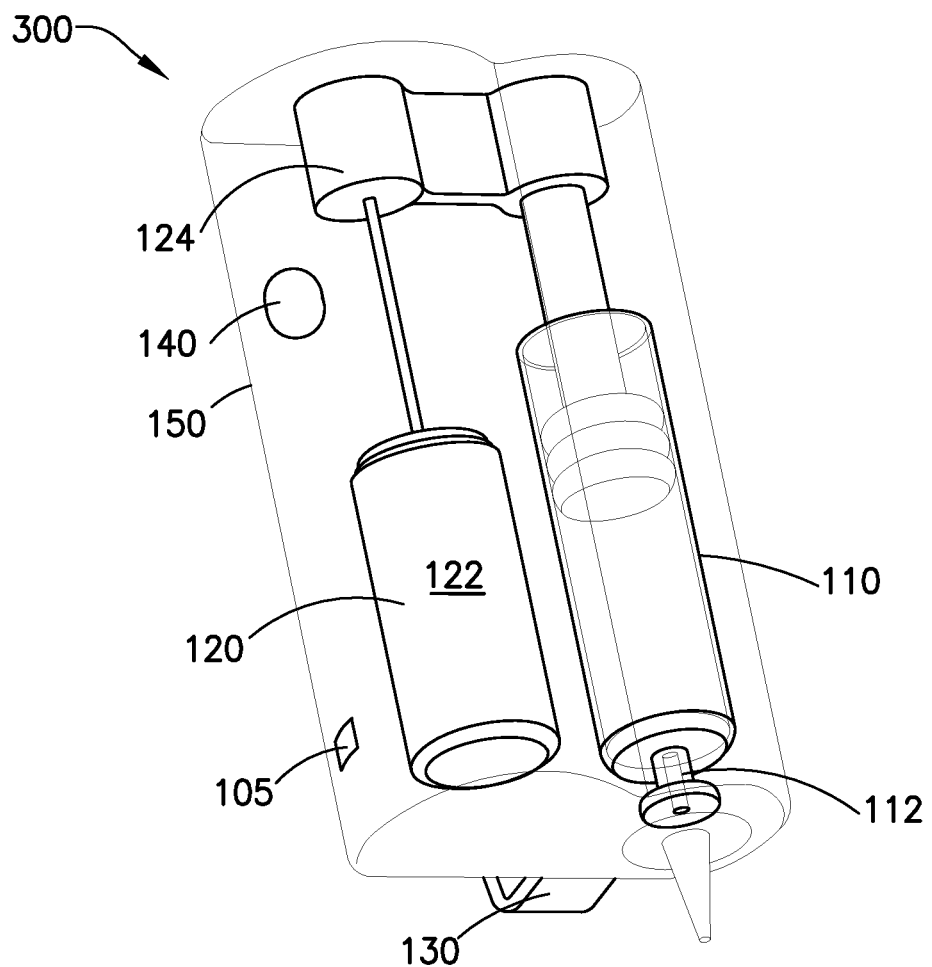
FIG. 3A is a perspective view of an injection device in accordance with an illustrative embodiment of the present invention.

FIGS. 3A-3D depict illustrative embodiments of an injection device 300 in accordance with the present invention. The injection device 300, as shown in FIG. 3A, includes a fluid container 110 having a fluid container exit port 112, an injection driving element 120, a connection module 130 and an injection trigger 140. The injection driving element 120 is adapted to displace fluid from the fluid container 110 through the fluid container exit port 112.

In an illustrative embodiment according to the present invention, the injection device 300 further includes a housing 150 partially or fully enclosing the fluid container 110 and the injection driving element 120.

In an illustrative embodiment according to the present invention, the connection module 130 is connectable to a mobile device. The connection module 130 is adapted to receive electrical power from the mobile device. The connection module 130 includes any wired or wireless mobile device connector known in the art able to transmit electrical power, including, but not limited to, USB, USB Mini-A, USB Mini-B, Micro-USB, 8-pin, 9-pin and 30-pin connectors, and electromagnetic couplings.

Figure 3B:
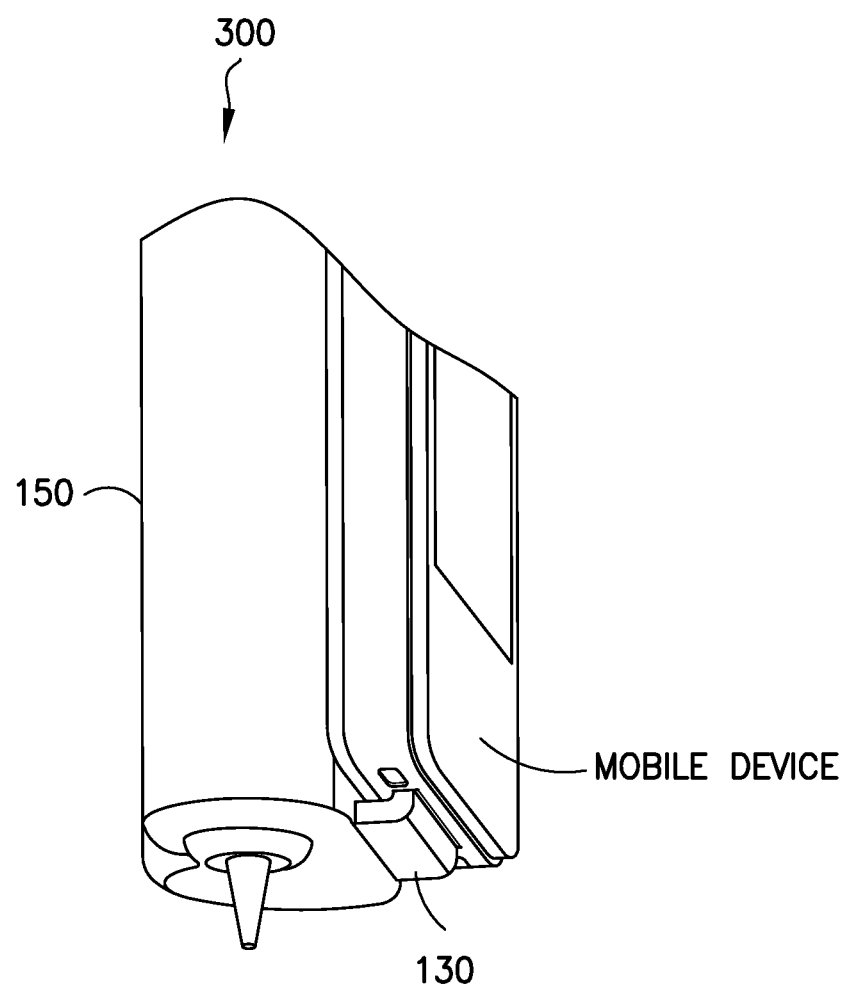
FIG. 3B is a perspective view of an injection device in combination with a mobile device, in accordance with an illustrative embodiment of the present invention.

In an illustrative embodiment according to the present invention, the mobile device is connected to the injection device 300 through a mount. In one embodiment, the mount is part of the connection module. Thus, the coupling of the connection module with the mobile device provides a structural coupling and allows a mating to occur between the injection device 300 and the mobile device. Structural coupling occurs when one or more elements are at least partially mated together. For example, a structural coupling may occur by mating, mounting, gripping, enclosing, adhering, locking, affixing, attaching, or any other way of physically connecting elements together. FIG. 3B shows an illustrative embodiment of an injection device 300 according to the present invention in combination with a mobile device. The connection module 130 is connected and coupled to a mobile device. FIG. 3B shows the connection module 130 engaging an electronic input port of the mobile device to structurally couple the mobile device with the injection device.

In an illustrative embodiment according to the present invention, the connection module 130 is electrically connected to the injection driving element 120, such that electrical power received from a mobile device powers the injection driving element 120 when the injection trigger 140 is activated. For example, if the mobile device is an Apple® iPhone®, the mobile device can provide direct current to the injection driving element 120 through an 8-pin or 30-pin port when the injection trigger 140 is activated.

In an illustrative embodiment according to the present invention, an injection device does not include an injection trigger 140. Rather, the injection driving element 120 is directly controlled by electrical signals, including, but not limited to digital or analog electrical signals from the mobile device through the connection module 130. These electrical signals can be generated using software in the mobile device. Thus, in this embodiment, the connection module 120 provides both a structural coupling and an electrical coupling.

In an illustrative embodiment according to the present invention, the injection trigger 140 includes any trigger known in the art, including, but not limited to, a depressible electrical button that is activated by depressing it and deactivated by releasing it. In an illustrative embodiment according to the present invention, the injection trigger 140 is a latch releasing mechanical button.

In operation of an illustrative embodiment according to the present invention, a user activates the injection trigger 140 to power the injection driving element 120. Activating the injection trigger 140 triggers the displacement of fluid from the fluid container 110 through the fluid container exit port 112.

In an illustrative embodiment according to the present invention in which the injection trigger 140 includes a depressible button that is activated by depressing it and deactivated by releasing it, a user can prime the injection device 300 before an injection. The user primes the injection device 300 by orienting the fluid container exit port 112 upward and activating the injection trigger 140 for a short period of time.

In an illustrative embodiment according to the present invention, the mobile device controls the motor of the injection device 300 according to injection parameters, for instance through a power management system controlled by software or hardware of the mobile device. Such motor control functions are managed by a computing/processing module of the mobile device. The injection process can thus be completely or partially controlled by the software and/or hardware of the mobile device. The mobile device provides real-time instructions on proper use of the device or other aspects of the treatment, feedback or confirmation on how the device was used, and results of disease specific physical and/or neurological functional tests, which can be provided using features on the mobile device, to quantify patient's disease state.

In an illustrative embodiment according to the present invention, as shown in FIG. 3A, the injection driving element 120 includes a motor 122. The motor 122 includes any electric motor known in the art, including, but not limited to, a brushed direct current (DC) electric motor, a brushless motor, a stepper motor, a servomotor, a gearmotor, a hollow shaft motor, or a shaftless motor. In an illustrative embodiment according to the present invention, the injection driving element 120 further includes a plunger element 124. The plunger element 124 is slidably displaceable within the fluid container 110 to displace fluid therein. The plunger element 124 is mechanically coupled to the motor 122, the motor 122 causing displacement of the plunger element 124 relative to the fluid container 110.

Figure 3C:
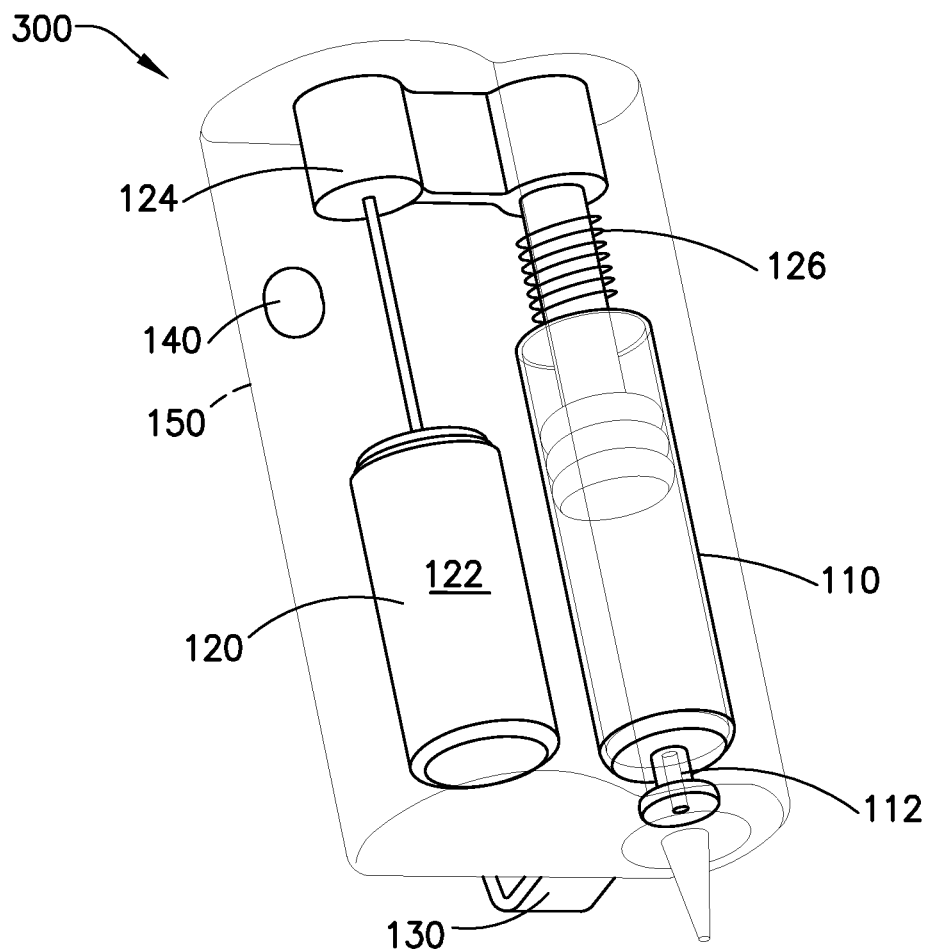
FIG. 3C is a perspective view of an injection device including a spring, in accordance with an illustrative embodiment of the present invention.

In an illustrative embodiment according to the present invention, as shown in FIG. 3C, an injection force is provided solely by or in conjunction with a mechanical component, such as a spring 126 or any other resilient component or mechanism known in the art. The motor 122 stresses the spring 126, and a relaxation of the spring 126 displaces the plunger 124 relative to the fluid container 110. The spring 126 can be kept in a stressed state using a mechanical stop, such as a latch. Disengaging the latch can trigger an injection by releasing the spring 126 into a relaxed state. In an illustrative embodiment according to the present invention wherein the injection trigger 140 is latch releasing mechanical button, the injection trigger 140 releases the plunger, which displaces fluid in the fluid container 110 by the injection force provided solely by or in conjunction with the spring 126.

Figure 3D:
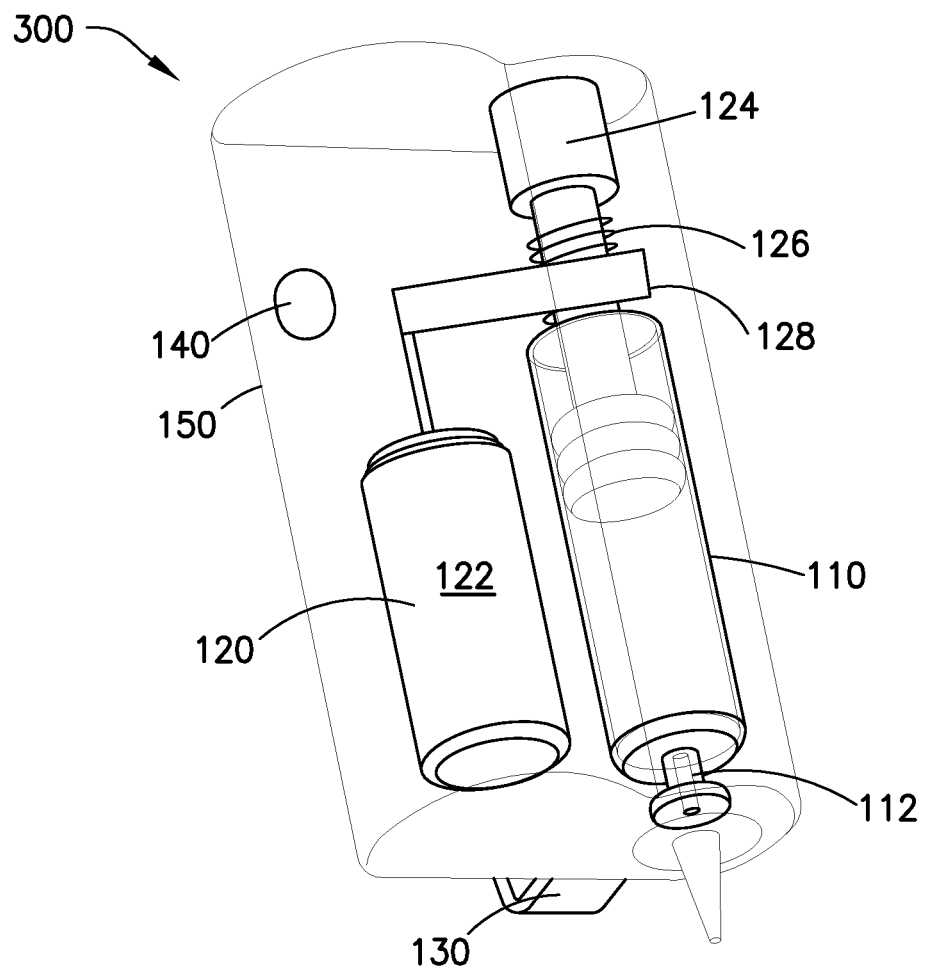
FIG. 3D is a perspective view of an injection device including a dose defining member, in accordance with an illustrative embodiment of the present invention.

In an illustrative embodiment according to the present invention, as shown in FIG. 3D, the injection driving element 120 further includes a dose defining member 128 coupled to the motor 122 and adapted to limit the displacement of the plunger element 124. In an illustrative embodiment according to the present invention, the motor 122 performs a dose dialing function by displacing the dose defining member 128 to a location determining the extent to which a dose will be expelled from the fluid container 110. The dose defining member 128 includes, but is not limited to, a mechanical stop, an optical or electromagnetic switch, an electrical sensor, a resistive circuit or a proximity switch. The actuation of the injection can be performed by another motor, by spring or manually. In an illustrative embodiment according to the present invention wherein the injection trigger 140 is latch releasing mechanical button, the injection trigger 140 releases the plunger, which displaces fluid in the fluid container 110 by the injection force provided solely by or in conjunction with a spring 126.

In an illustrative embodiment according to the present invention, the injection driving element 120 compresses the fluid container 110 to displace fluid therein.

In an illustrative embodiment according to the present invention, the injection driving element 120 includes any suitable pump member that can be driven by a motor, including, but not limited to, piston pumps and diaphragm pumps.

In an illustrative embodiment according to the present invention, the injection driving element 120 includes any fluid pump known in the art, including, but not limited to, a piezo-driven pump, an electromagnetic pump, an electrochemical pump, a thermo-pneumatic pump, a shape memory alloy pump, or an electrostatic pump.

In an illustrative embodiment according to the present invention, the housing 150 includes a molded plastic enclosure, which is inexpensive and lightweight, making the injection device 300 affordable and portable.

In an illustrative embodiment according to the present invention, fluid communication out of the fluid container exit port 112 is performed using any desired injection or infusion method known in the art for delivering fluid to an administration site, including, but not limited to, using needle adapters or needles, or using needleless delivery systems.

In an illustrative embodiment according to the present invention, the fluid container 110 includes a prefillable or prefilled medicament cartridge, which can be fitted into the housing 150, and from which a desired dose, full or partial, is delivered. In an illustrative embodiment according to the present invention, the cartridge is made of glass or polymer, and performs as a long term storage and as an injection container.

In an illustrative embodiment according to the present invention, the injection device 300 can be disposed after full dose administration. A disposable injection device can be desired for administrations of expensive drugs. In an illustrative embodiment according to the present invention, the fluid container 110 can be disposed after full dose administration. In an illustrative embodiment according to the present invention, the fluid container 110 can be refilled for future injections.

In an illustrative embodiment according to the present invention, the injection device 300 further includes a sensor 105 (as shown in FIG. 3A), adapted to sense identification information. The sensor 105 can include any identification sensor known in the art, including, but not limited to, a camera, a barcode reader, a Quick Response (QR) code reader, a Radio-Frequency Identification (RFID) tag reader, a Near-Field Communication (NFC) tag reader, or a label reader. In an illustrative embodiment according to the present invention, a processor performs a medicament identification function using data gathered by the sensor 105. In an illustrative embodiment according to the present invention, a processor performs a needle identification function using data gathered by the sensor 105.

In an illustrative embodiment according to the present invention, injection-related information is obtained using an injection-related information sensor of the mobile device, of the injection device, or of an external device connected to the mobile device. Injection-related information includes, but is not limited to, dose, dose administration speed, needle insertion depth, needle insertion location, needle insertion time, injection pressure, and temperature at injection site.

Figure 4A:
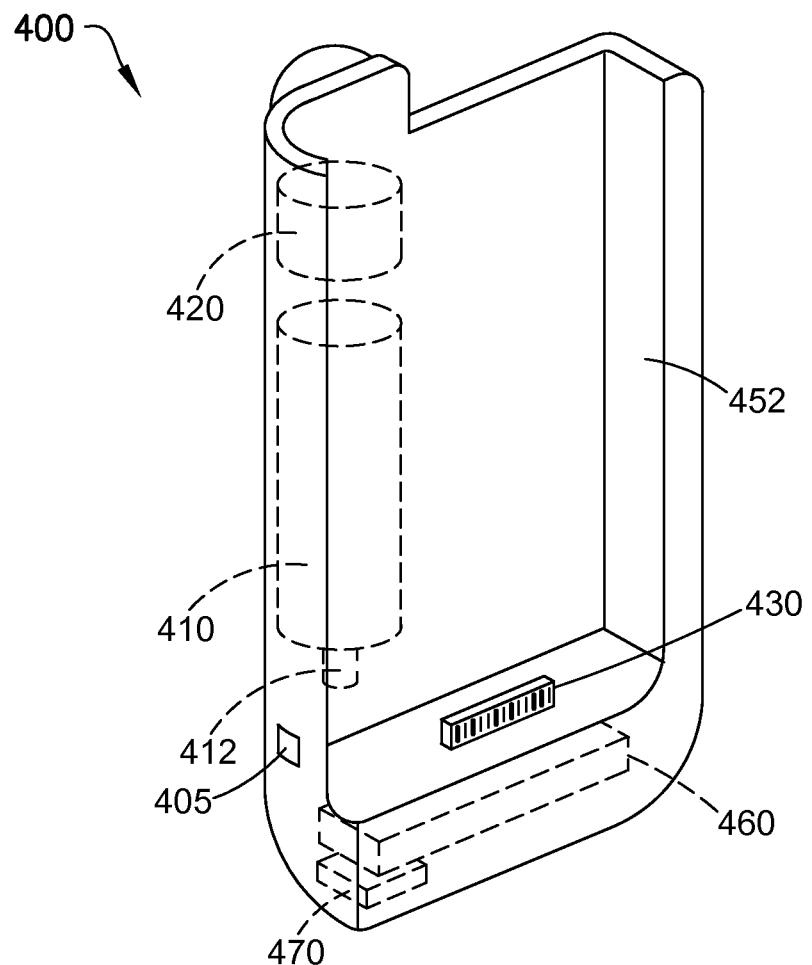
FIG. 4A is a schematic view of an injection device with a housing sleeve in accordance with an illustrative embodiment of the present invention.

FIGS. 4A-4D depict illustrative embodiments of an injection device 400 in accordance with the present invention. As shown in FIG. 4A, the injection device 400 includes a fluid container 410 having a fluid container exit port 412, an injection driving element 420, a connection module 430, a controller interface 460 and a battery 470. The injection driving element 420 is adapted to displace fluid from the fluid container 410 through the fluid container exit port 412.

In an illustrative embodiment according to the present invention, the injection device 400 further includes a housing 450 partially or fully enclosing the fluid container 410, the injection driving element 420, the controller interface 460 and the battery 470. In an illustrative embodiment according to the present invention, the injection device 400 further includes a housing sleeve 452 that is adapted to receive and mount the mobile device. Thus, in this embodiment the mount is a housing sleeve configured to mate with and hold the mobile device. The housing sleeve 452 can be adapted or configured to provide a structural coupling between the injection device 400 and the mobile device. In an illustrative embodiment according to the present invention, the housing 450 and the housing sleeve 452 may be one continuous piece. In another illustrative embodiment according to the present invention, the housing 450 and the housing sleeve 452 may be separate pieces. A separate housing 450 and housing sleeve 452 may be structurally coupled. The housing 450 and housing sleeve 452 can thereby provide structural integrity to a combination of an injection device and a mobile device, by providing a substantial area of contact between the injection device 400 and the mobile device.

It should be realized in this embodiment that the housing sleeve 452 can be adapted to receive a bare mobile device or alternatively one that is fitted in a cover or case. The housing sleeve 452 may have one or more pieces that can separately, partially or fully enclose one or more of the fluid container 410, the injection driving element 420, the controller interface 460, the battery 470, and a mobile device.

In an illustrative embodiment according to the present invention, the housing sleeve 452 is adapted to partially or completely cover a mobile device or mobile device cover or case. In an illustrative embodiment according to the present invention, the housing sleeve 452 is further adapted to partially or completely grasp the mobile device or mobile device cover or case so that the mobile device is maintained within the housing sleeve during normal use. The housing sleeve 452 can restrict movement of the mobile device or hold the mobile device in place.

In an illustrative embodiment according to the present invention, the housing sleeve 452 is adapted to include openings for access to mobile device features including, but not limited to, buttons, keyboards, screens, interfaces, plugs, jacks, sockets, speakers, and cameras. In an illustrative embodiment according to the present invention, the housing sleeve 452 is further adapted to include room for wires, cords, or other connection elements to the mobile device.

In an illustrative embodiment according to the present invention, the housing sleeve 452 is adapted to partially or fully cover a mobile device in a transparent material to allow visual access. In an illustrative embodiment according to the present invention, the housing sleeve 452 is adapted to partially or fully cover a mobile device in material that maintains touch screen functionality. In an illustrative embodiment according to the present invention, the housing sleeve 452 is adapted to partially or fully cover a mobile device in a flexible material to allow for depression of buttons and other mobile device features. In an illustrative embodiment according to the present invention, the housing sleeve 452 is adapted to include one or more flaps that partially or fully cover mobile device features. The flaps can be moved to allow access to those features. In an illustrative embodiment according to the present invention, the housing sleeve 452 is adapted to partially or fully cover a mobile device in a material that will allow for some passage of sound.

In an illustrative embodiment according to the present invention, the housing sleeve 452 is adapted to include a soft, durable shell that partially or fully encloses a mobile device. In an illustrative embodiment according to the present invention, the housing sleeve 452 is adapted to include, either alone or in combination with a soft shell, a hard shell that partially encloses a mobile device. In an illustrative embodiment according to the present invention, the housing sleeve 452 is adapted to include one or more soft or hard shell pieces that cover part of a mobile device. In an illustrative embodiment according to the present invention, the housing sleeve 452 can partially or completely protect the phone from one or more of dirt, dust, liquids, stains, smudges, scratches, dents, cracks, or other hazards.

In an illustrative embodiment according to the present invention, the housing sleeve 452 includes one or more of protrusions, ridges, recesses, curves, edges, lips, openings, rough surfaces, or other physical features to facilitate gripping the injection device 400.

Figure 4B:
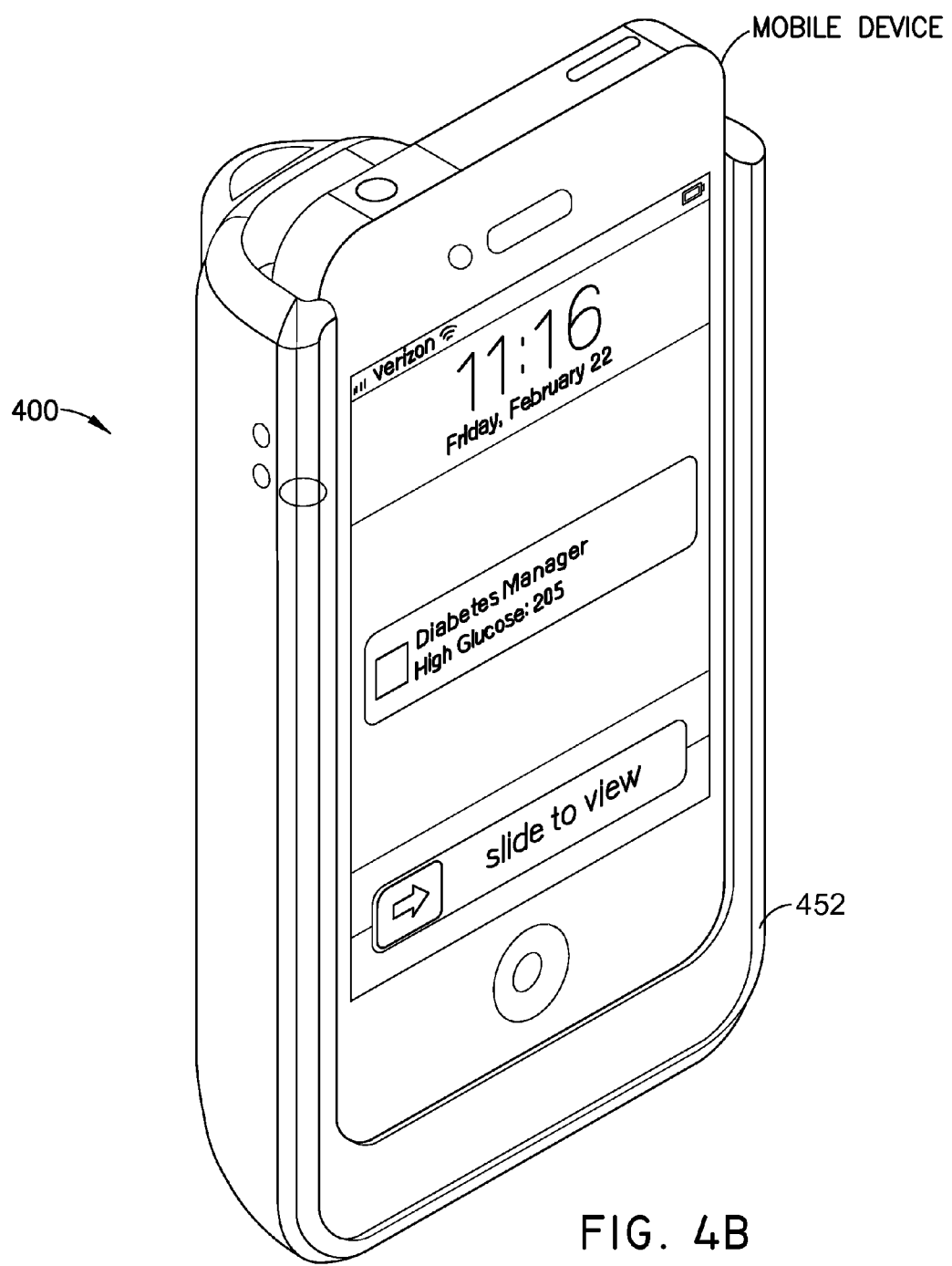
FIGS. 4B and 4C show the injection device of FIG. 4A in combination with a mobile device, in accordance with an illustrative embodiment of the present invention.

FIG. 4B shows an illustrative embodiment of an injection device 400 according to the present invention in combination with a mobile device. The housing sleeve 452 provides the mobile device with structural protection at least from lateral and dorsal impact, and partial structural protection from frontal impact.

Figure 4C:
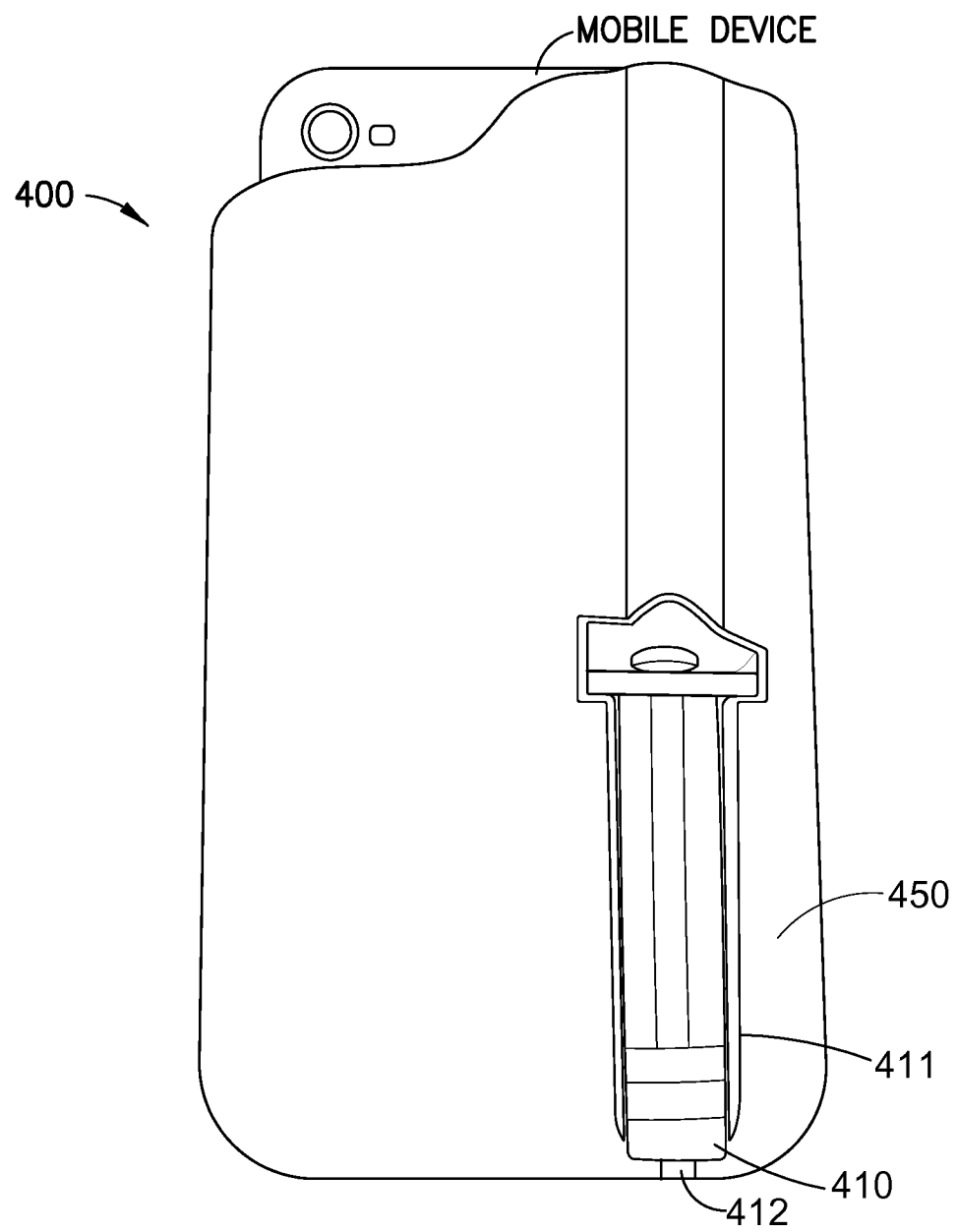

FIG. 4C shows an illustrative embodiment of an injection device 400 according to the present invention in combination with a mobile device. The housing 450 provides an opening 411 for access to the fluid container 410. The opening 411 can allow for identifying a medicament in the fluid container 410, for viewing a medicament fluid level of the fluid container 410, or for removing and replacing the fluid container 410.

In an illustrative embodiment according to the present invention, the housing 450 is adapted for housing a second battery, and/or any number of sensors of patient vital data. Patient vital data includes, but is not limited to, blood pressure, temperature, blood oxygen level, electrical activity of the heart, cholesterol, or blood glucose level, and can be used by a mobile device for injection or treatment-related calculations, or can be communicated to an external device by the mobile device. Sensors of patient vital data may include, but are not limited to, a thermometer, a BGM, a pulse oximeter, a blood pressure sensor, a cholesterol tester, and an Electrocardiography ("ECG") device. In an illustrative embodiment according to the present invention, the injection device 400 can report to the mobile device on the status of the delivery, including, but not limited to, full dose administration. Delivery status can be measured using a delivery sensor, including, but not limited to, an electric eye or a flow sensor, or using a penetration sensor.

In an illustrative embodiment according to the present invention, the connection module 430 is connectable to a mobile device. In an illustrative embodiment according to the present invention, the connection module 430 includes any wired or wireless mobile device connector known in the art, including, but not limited to, USB, USB Mini-A, USB Mini-B, Micro-USB, 8-pin, 9-pin and 30-pin connectors, and electromagnetic couplings. In an illustrative embodiment according to the present invention, the connection module 430 includes any wireless connection module connectable to a mobile device known in the art, including, but not limited to, radio frequency, Bluetooth®, infrared, Wi-Fi or cellular connection modules.

In an illustrative embodiment according to the present invention, the battery 470 provides electrical power to the injection driving element 420. The battery 470 can be rechargeable or disposable. In an illustrative embodiment according to the present invention, the connection module 430 is adapted provide electrical power from a mobile device to the injection driving element 420.

In an illustrative embodiment according to the present invention, the controller interface 460 is adapted to receive a signal from the mobile device through the connection module 430. In an illustrative embodiment according to the present invention, the controller interface 430 translates digital or analog electrical signals input from a mobile device through the connection module 430, into electric signals, including, but not limited to, digital or analog electrical signals output to the injection driving element 420. In an illustrative embodiment according to the present invention, signals are indicative of control commands for a motor, including, but not limited to, a start command, a stop command, a direction command, and a speed command. In an illustrative embodiment according to the present invention, the controller interface 460 is adapted for a specific type of injection driving element 420. Using the controller interface 460 can avoid relying on capabilities of the mobile device to directly control an injection driving element.

In an illustrative embodiment according to the present invention, the injection driving element 420 includes a motor. The motor includes any electric motor known in the art for this type of application, including, but not limited to, a brushed DC electric motor, a brushless motor, a stepper motor, a servomotor, a gearmotor, a hollow shaft motor, or a shaftless motor. In an illustrative embodiment according to the present invention, the injection driving element 420 further includes a plunger element. The plunger element is slidably displaceable within the fluid container 410 to displace fluid therein. The plunger element is mechanically coupled to the motor, the motor causing displacement of the plunger element relative to the fluid container 410.

Figure 4D:
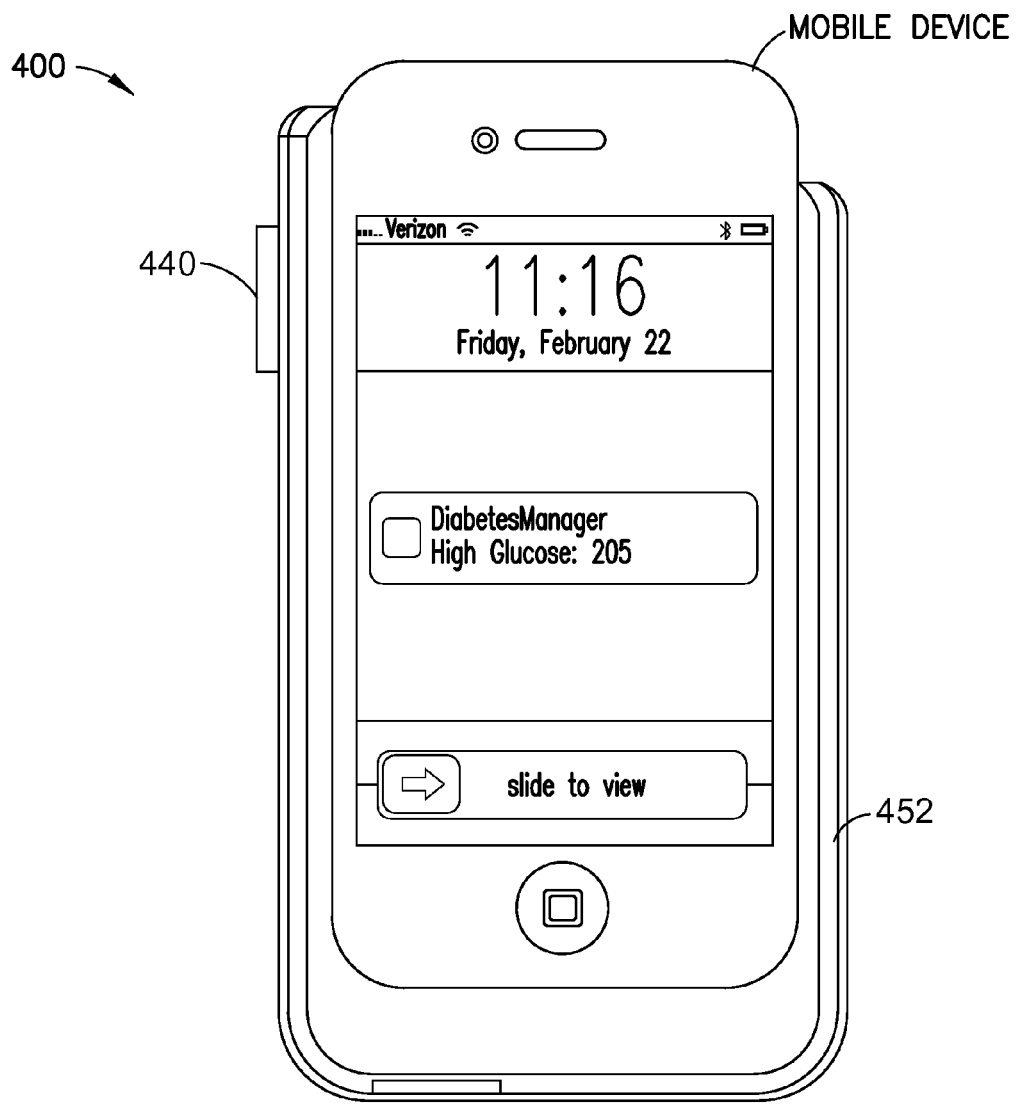
FIG. 4D shows the injection device of FIG. 4A including a spring, in combination with a mobile device, in accordance with an illustrative embodiment of the present invention.

In an illustrative embodiment according to the present invention, an injection force is provided solely by or in conjunction with a mechanical component, such as a spring. The motor stresses the spring, and a relaxation of the spring displaces the plunger relative to the fluid container 410. The spring can be kept in a stressed state using a mechanical stop, such as a latch. Disengaging the latch can trigger an injection by releasing the spring into a relaxed state. In an illustrative embodiment according to the present invention, as shown in FIG. 4D, the injection device 400 further includes an injection trigger 440 including a latch releasing mechanical button, which releases the plunger, which in turn displaces fluid in the fluid container 410 by the injection force provided solely by or in conjunction with the spring.

In an illustrative embodiment according to the present invention, as the injection driving element 420 further includes a dose defining member coupled to the motor and adapted to limit the displacement of the plunger element. In an illustrative embodiment according to the present invention, the motor performs a dose dialing function by displacing the dose defining member to a location determining the extent to which a dose will be expelled from the fluid container 410. The dose defining member includes, but is not limited to, a mechanical stop, an optical or electromagnetic switch, an electrical sensor, a resistive circuit or a proximity switch. The actuation of the injection can be performed by another motor, by spring or manually. In an illustrative embodiment according to the present invention wherein the injection trigger 440 is latch releasing mechanical button, the injection trigger 440 releases the plunger, which displaces fluid in the fluid container 410 by the injection force provided solely by or in conjunction with a spring.

In an illustrative embodiment according to the present invention, the injection driving element 420 compresses the fluid container 410 to displace fluid therein.

In an illustrative embodiment according to the present invention, the injection driving element 420 includes any suitable pump member that can be driven by a motor, including, but not limited to, piston pumps and diaphragm pumps.

In an illustrative embodiment according to the present invention, the injection driving element 420 includes any fluid pump known in the art, including, but not limited to, a piezo-driven pump, an electromagnetic pump, an electrochemical pump, a thermo-pneumatic pump, a shape memory alloy pump, or an electrostatic pump.

In an illustrative embodiment according to the present invention, the housing 450 and sleeve housing 452 include a molded plastic enclosure, which is inexpensive and lightweight, making the injection device 400 affordable and portable.

In an illustrative embodiment according to the present invention, fluid communication out of the fluid container exit port 412 is performed using any desired injection or infusion method known in the art for delivering fluid to an administration site, including, but not limited to, using needle adapters or needles, or using needleless delivery systems.

In an illustrative embodiment according to the present invention, the injection device 400 further includes an ON/OFF switch electrically coupled to the battery 470. An ON/OFF switch can avoid drawing power from the battery 470 when the injection device 400 is not being used.

In an illustrative embodiment according to the present invention, a displacement of fluid from the fluid container 410 through the fluid container exit port 412 is actuated in accordance with, or by an amount in accordance with, a signal received from a mobile device. In an illustrative embodiment according to the present invention, a signal received from the mobile device is generated by the mobile device in accordance with user input, patient vital data from the injection device 400, or patient vital data from an external device, including, but not limited to a CGM or other BGM. In an illustrative embodiment according to the present invention, the injection device 400 may further include a sensor for patient vital data, including, but not limited to a BGM.

In an illustrative embodiment according to the present invention, the injection device 400 receives a signal from a mobile device indicative of an injection. Receiving the signal received from a mobile device triggers an actuation of a motor that drives the injection by an amount in accordance with the signal received from a mobile device. In an illustrative embodiment according to the present invention, receiving the signal received from a mobile device triggers an actuation of a motor that drives a dose defining member in accordance with, or by an amount in accordance with, a signal received from a mobile device.

In an illustrative embodiment according to the present invention, as shown in FIG. 4D, the injection device 400 further includes an injection trigger 440, which includes any trigger known in the art, including, but not limited to, a depressible electrical button that is activated by depressing it and deactivated by releasing it. In an illustrative embodiment according to the present invention, the injection trigger 440 is a latch releasing mechanical button.

In operation of an illustrative embodiment according to the present invention, a user activates the injection trigger 440 to trigger the displacement of fluid from the fluid container 410 through the fluid container exit port 412 in accordance with, or by an amount in accordance with, a signal received from a mobile device. In an illustrative embodiment according to the present invention, activating the injection trigger 440 triggers the actuation of a motor that drives the injection in accordance with, or by an amount in accordance with, a signal received from a mobile device. In an illustrative embodiment according to the present invention, the actuation of a motor that drives a dose defining member in accordance with, or by an amount in accordance with, a signal received from a mobile device is first triggered by the mobile device. Activating the injection trigger 440 then triggers the actuation of the injection by an amount in accordance with the signal received from the mobile device.

In an illustrative embodiment according to the present invention, the injection device 400 is adapted for manual injection. Manual injection can provide a backup method of injection, for example, to allow a user to perform an injection in the event that a mobile device battery is depleted or otherwise unusable.

In an illustrative embodiment according to the present invention, a user can prime the injection device 400 before an injection. The user begins priming the injection device 400 by orienting the injection device 400, and therefore the fluid container exit port 412, upward. The rotation of the injection device 400 to a different orientation may be sensed by a sensor, such as an accelerometer or other rotational sensor within the injection device 400. This rotation of the fluid exit port to the upward position may allow air to rise to the top of the device and any needle that is present. Thus, detecting the rotation of the fluid exit port to the predetermined orientation wherein the fluid exit port faces upwards is included in aspects of the invention. Of course, other predetermined orientations of the injection device are also contemplated. Once the fluid exit port has rotated to the upwards orientation, the user can then tap on a medicament reservoir to cause any air bubbles left to rise.

In an illustrative embodiment according to the present invention, a mobile device can display an instruction to a user to tap on a medicament reservoir. Once the injection device has been detected to be in oriented with the fluid container exit port 412 upward, the injection system can then enable an input such as a priming button or trigger. The user then executes a priming function using, for example, a touchscreen on a mobile device connected to the injection device by selecting or activating the priming button or trigger. In one aspect, the input is a graphical button that becomes enabled on a touchscreen of the mobile device. The priming function then causes the injection device to prime, wherein the air is forced out of the fluid container exit port 412 by the liquid.

In an illustrative embodiment according to the present invention, the fluid container 410 includes a prefillable or prefilled medicament cartridge, which can be fitted into the housing 450, and from which a desired dose, full or partial, is delivered. In an illustrative embodiment according to the present invention, the cartridge is made of glass or polymer, and performs as a long term storage and as an injection container.

In an illustrative embodiment according to the present invention, the fluid container 410 can be disposed after full dose administration. The fluid container 410 can then be replaced. In an illustrative embodiment according to the present invention, the fluid container 410 can be refilled for future injections. In an illustrative embodiment, the event of disposing the fluid container can be, for example, electromechanically or magnetically recorded and used in subsequent analysis.

In an illustrative embodiment according to the present invention, the injection device 400 further includes a sensor 405 (as shown in FIG. 4A), adapted to sense identification information. The sensor 405 can include any identification sensor known in the art, including, but not limited to, a camera, a barcode reader, a Quick Response (QR) code reader, a Radio-Frequency Identification (RFID) tag reader, a Near-Field Communication (NFC) tag reader, or a label reader. In an illustrative embodiment according to the present invention, a processor performs a medicament identification function using data gathered by the sensor 405. In an illustrative embodiment according to the present invention, a processor performs a needle identification function using data gathered by the sensor 405.

In an illustrative embodiment according to the present invention, injection-related information is obtained using an injection-related information sensor of the mobile device, of the injection device, or of an external device connected to the mobile device. Injection-related information includes, but is not limited to, dose, dose administration speed, needle insertion depth, needle insertion location, needle insertion time, injection pressure, and temperature at injection site.

Figure 5A:
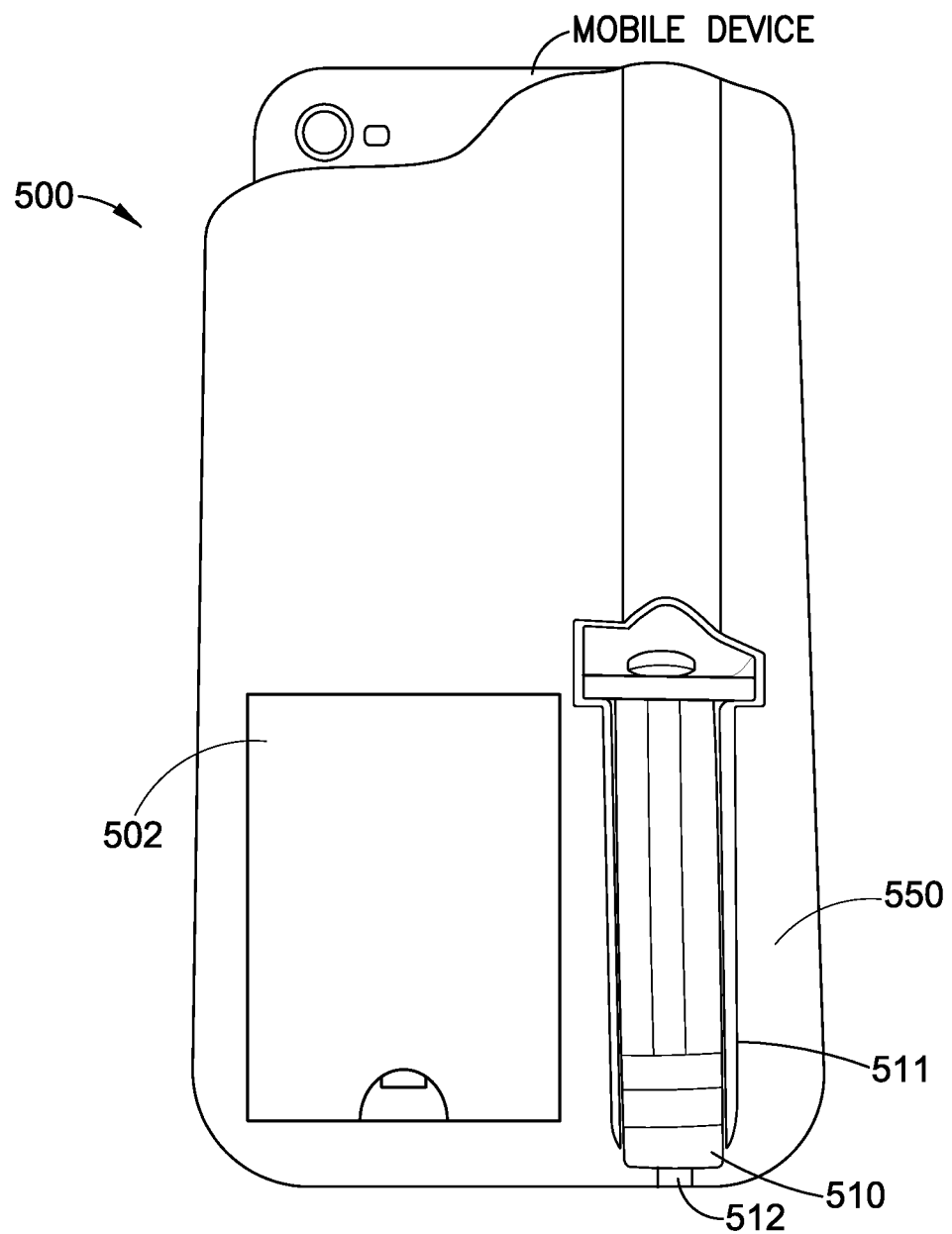
FIGS. 5A and 5B depict alternative embodiments of an injection device in accordance with the present invention
Figure 5B:
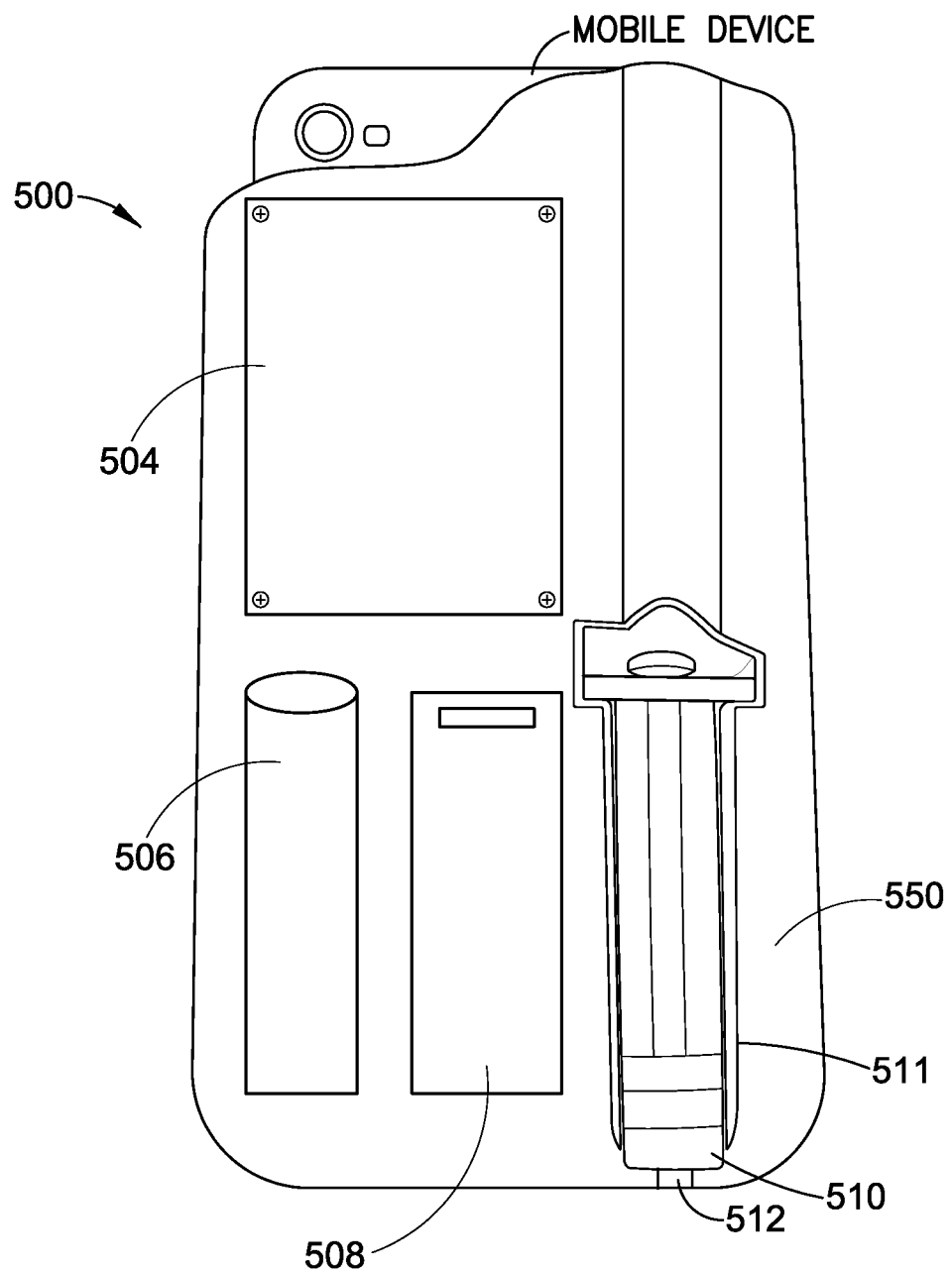

FIGS. 5A-5B depict illustrative embodiments of an injection device 500 in accordance with the present invention. As shown in FIG. 5A, the injection device 500 includes a fluid container 510 having a fluid container exit port 512, a housing 550, and an opening 511 for access to the fluid container 510. In an illustrative embodiment according to the present invention, injection device 500 contains at least some of the same components as injection device 400.

In an illustrative embodiment according to the present invention, as shown in FIG. 5A, the injection device 500 further includes a sensor 502 of patient vital data. The sensor 502 may be adapted to communicate the patient vital data to the mobile device via a wireless or wired connection. Patient vital data may include, but is not limited to, blood pressure, temperature, blood oxygen level, electrical activity of the heart, cholesterol, or blood glucose level. These data can be used by the mobile device for injection or treatment-related calculations, or can be communicated to an external device by the mobile device. It should be appreciated that the sensor 502 may include, but is not limited to, a thermometer, a blood glucose monitor (BGM), a pulse oximeter, a blood pressure sensor, a cholesterol tester or an Electrocardiography ("ECG") device. For example, if the sensor is a BGM, then it could be configured so that a disposable test strip containing a drop of patient blood can be inserted into a sensor 502 to monitor blood glucose levels. The mobile device could then read the data transmitted from the BGM in the device 500 and provide an accurate, real-time analysis of the blood glucose levels found in the blood placed on the test strip.

In an illustrative embodiment according to the present invention, as shown in FIG. 5B, the injection device 500 includes a battery housing 504. The battery housing 504 allows for the storage of a second battery that can be used to extend the amount of power provided to the mobile device.

In an illustrative embodiment according to the present invention, as shown in FIG. 5B, the injection device 500 includes auxiliary compartments 506 and 508. In an illustrative embodiment according to the present invention, the auxiliary compartments 506 and 508 can store one or more items including, but not limited to, needles, pills, test strips, and wipes. The auxiliary compartment 506 may have a tubular structure configured to store needles for injection. In an illustrative embodiment according to the present invention, the auxiliary compartment 508 can include, but is not limited to, a hinged door or sliding door. In an illustrative embodiment according to the present invention, the injection device 500 can sense and report to the mobile device on the status of the auxiliary compartments 506 and 508, including, but not limited to, the amount of the items in a compartment, the times when items are removed, and the amount of items removed.

The components of the illustrative devices, systems and methods employed in accordance with the illustrated embodiments of the present invention can be implemented, at least in part, in digital electronic circuitry, analog electronic circuitry, or in computer hardware, firmware, software, or in combinations of them. These components can be implemented, for example, as a computer program product such as a computer program, program code or computer instructions tangibly embodied in an information carrier, or in a machine-readable storage device, for execution in accordance with, or to control the operation of, data processing apparatus such as a programmable processor, a computer, or multiple computers. Examples of the computer-readable recording medium include, but are not limited to, read-only memory (ROM), random-access memory (RAM), CD-ROMs, magnetic tapes, floppy disks, optical data storage devices. It is envisioned that aspects of the present invention can be embodied as carrier waves (such as data transmission through the Internet via wired or wireless transmission paths). A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network. The computer-readable recording medium can also be distributed over network-coupled computer systems so that the computer-readable code is stored and executed in a distributed fashion. Also, functional programs, codes, and code segments for accomplishing the present invention can be easily construed as within the scope of the invention by programmers skilled in the art to which the present invention pertains. Method steps associated with the illustrative embodiments of the present invention can be performed by one or more programmable processors executing a computer program, code or instructions to perform functions (e.g., by operating on input data and/or generating an output). Examples of program instructions include both machine code, such as produced by a compiler, and files containing higher level code that may be executed by the computer using an interpreter. The described hardware devices may be configured to act as one or more software modules in order to perform the operations of the above-described embodiments of the present invention. Method steps can also be performed in accordance with, and apparatus of the invention can be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example, semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented in accordance with, or incorporated in special purpose logic circuitry.

Although only a few illustrative embodiments of the present invention have been described in detail above, those skilled in the art will readily appreciate that many modifications are possible in the illustrative embodiments, and various combinations of the illustrative embodiments are possible, without materially departing from the novel teachings and advantages of this invention. Accordingly, all such modifications are intended to be included within the scope of this invention.

What is claimed is:

1. An injection device, comprising:
   an injection driving element capable of displacing fluid from a fluid container through a fluid container exit port, wherein the injection driving element comprises a motor;
   a housing sleeve having a rear wall, a first side wall, a second side wall, and a bottom wall defining a chamber for receiving a mobile device, wherein the housing sleeve is configured to at least partially enclose a rear surface, two side surfaces, and a bottom surface of the mobile device when the mobile device is received within the chamber, wherein the rear wall of the housing sleeve at least partially encloses the injection driving element and fluid container;
   a connection module electrically connected to the injection driving element and configured to receive electrical power and data from the mobile device, and wherein the motor is adapted to displace the fluid relative to the fluid container in accordance with, or by an amount in accordance with a signal received at the connection module from the mobile device.

2. The injection device of claim 1, wherein a portion of the connection module is adapted to mate with the mobile device.

3. The injection device of claim 1, wherein the connection module is further adapted to power the injection driving element with the electrical power received from the mobile device.

4. The injection device of claim 1, wherein the injection driving element comprises a plunger element mechanically coupled to the motor.

5. The injection device of claim 4, wherein the motor is adapted to cause displacement of the plunger element relative to the fluid container in accordance with, or by an amount in accordance with a signal received from the mobile device.

6. The injection device of claim 1, further comprising a controller interface adapted to receive a signal from the mobile device through the connection module.

7. The injection device of claim 6, wherein the controller interface translates digital or analog electrical signals input from the mobile device through the connection module, into electric signals output to the injection driving element.

8. The injection device of claim 7, wherein the electrical signals output to the injection driving element comprise at least one control command for a motor.

9. The injection device of claim 1, further comprising a fluid container having a fluid container exit port.

10. The injection device of claim 9, wherein the fluid container comprises a prefillable or prefilled fluid cartridge adapted to be fitted into the housing.

11. The injection device of claim 1, further comprising a sensor of patient data.

12. The injection device of claim 1, further comprising a sensor of injection-related information.

13. The injection device of claim 1, further comprising an identification sensor.

14. The injection device of claim 13, wherein the injection device is adapted to communicate information from the identification sensor to the mobile device.

15. The injection device of claim 1, further comprising one or more auxiliary compartments.

16. The injection device of claim 15, wherein the injection device is adapted to communicate information about the auxiliary compartments to the mobile device.

17. A combination, comprising:
    the injection device of claim 1; and
    the mobile device connected to the injection device and at least partially enclosed by the sleeve.

18. The combination of claim 17, wherein the mobile device comprises:
    a power module adapted to provide power to the injection driving element of the injection device; and
    a computing module.

19. The combination of claim 17, wherein the motor of the injection device is adapted to operate according to instructions by the computing module of the mobile device.

20. The combination of claim 17, wherein the mobile device further comprises:
    a mobile device connection module connectable to the connection module of the injection device,
    wherein the mobile device connection module is adapted to connect the injection driving element of the injection device to at least one from the set of the power module and the computing module.

21. The combination of claim 17, wherein the mobile device is adapted to adjust or modulate injection parameters and monitor injection diagnostics.

22. The combination of claim 17, wherein the injection device is adapted to report to the mobile device on a status of delivery.

23. The combination of claim 17, wherein the mobile device further comprises a communication module connectable to a network.

24. The combination of claim 23, wherein the communication module is adapted to communicate injection, treatment or patient related data to an external device.

25. An injection system, comprising:
    a mobile device; and
    an injection device comprising:
    a fluid container having a fluid container exit port;

an injection driving element capable of displacing fluid from the fluid container through the fluid container exit port, wherein the injection driving element comprises:
  a motor; and
  a plunger element mechanically coupled to the motor wherein the motor is adapted to cause displacement of the plunger relative to the fluid container in accordance with, or by an amount in accordance with a signal received from the mobile device;
a housing sleeve having a rear wall, a first side wall, a second side wall, and a bottom wall defining a chamber for receiving the mobile device, wherein the housing sleeve is configured to at least partially enclose a rear surface, two side surfaces, and a bottom surface of the mobile device when the mobile device is received within the chamber, wherein the rear wall of the housing sleeve at least partially encloses the injection driving element and fluid container.

26. The injection system of claim 25, further comprising an identification sensor positioned on an exterior surface of the housing sleeve.

27. The injection system of claim 25, further comprising a connection module electrically connected to the injection driving element and configured to mate with the mobile device, wherein the connection module is configured to receive electrical power and data from the mobile device.

28. The injection system of claim 25, further comprising a controller interface adapted to receive a signal from the mobile device through the connection module.

* * * * *